(12) United States Patent
Smithwick et al.

(10) Patent No.: US 11,675,429 B2
(45) Date of Patent: Jun. 13, 2023

(54) CALIBRATION, CUSTOMIZATION, AND IMPROVED USER EXPERIENCE FOR BIONIC LENSES

(71) Applicant: DISNEY ENTERPRISES, INC., Burbank, CA (US)

(72) Inventors: Quinn Y. J. Smithwick, Pasadena, CA (US); Jon H. Snoddy, Pasadena, CA (US); Douglas A. Fidaleo, Santa Clarita, CA (US)

(73) Assignee: Disney Enterprises, Inc., Burbank, CA (US)

( * ) Notice: Subject to any disclaimer, the term of this patent is extended or adjusted under 35 U.S.C. 154(b) by 0 days.

(21) Appl. No.: 17/399,245

(22) Filed: Aug. 11, 2021

(65) Prior Publication Data
US 2021/0373660 A1    Dec. 2, 2021

Related U.S. Application Data

(62) Division of application No. 16/455,012, filed on Jun. 27, 2019, now Pat. No. 11,099,641.

(51) Int. Cl.
| | |
|---|---|
| G06F 3/01 | (2006.01) |
| A61B 3/103 | (2006.01) |
| A61B 3/117 | (2006.01) |
| G06T 7/521 | (2017.01) |
| G02C 7/04 | (2006.01) |
| A61B 3/125 | (2006.01) |

(52) U.S. Cl.
CPC .............. *G06F 3/013* (2013.01); *A61B 3/103* (2013.01); *A61B 3/1173* (2013.01); *A61B 3/125* (2013.01); *G02C 7/04* (2013.01); *G06F 3/012* (2013.01); *G06T 7/521* (2017.01); *G06T 2207/30201* (2013.01)

(58) Field of Classification Search
None
See application file for complete search history.

(56) References Cited

U.S. PATENT DOCUMENTS

| | | | |
|---|---|---|---|
| 9,654,674 B1* | 5/2017 | Wiser | H04N 23/66 |
| 2008/0291317 A1 | 11/2008 | Endo et al. | |
| 2010/0165093 A1 | 7/2010 | Sugio et al. | |
| 2011/0170059 A1 | 7/2011 | Ehrmann et al. | |
| 2014/0194710 A1 | 7/2014 | Ho et al. | |
| 2016/0029883 A1 | 2/2016 | Cox | |
| 2017/0336641 A1* | 11/2017 | von und zu Liechtenstein | G06T 19/006 |
| 2018/0053056 A1 | 2/2018 | Rabinovich et al. | |
| 2018/0239144 A1 | 8/2018 | Woods et al. | |
| 2018/0246330 A1* | 8/2018 | Fattal | G02B 6/0058 |
| 2021/0072821 A1* | 3/2021 | von und zu Liechtenstein | G06F 3/012 |

* cited by examiner

*Primary Examiner* — Talha M Nawaz

(74) *Attorney, Agent, or Firm* — Dorsey & Whitney LLP

(57) ABSTRACT

The present disclosure relates to calibration, customization, and improved user experiences for smart or bionic lenses that are worn by a user. The calibration techniques include detecting and correcting distortion of a display of the bionic lenses, as well as distortion due to characteristics of the lens or eyes of the user. The customization techniques include utilizing the bionic lenses to detect eye characteristics that can be used to improve insertion of the bionic lenses, track health over time, and provide user alerts. The user experiences include interactive environments and animation techniques that are improved via the bionic lenses.

19 Claims, 16 Drawing Sheets

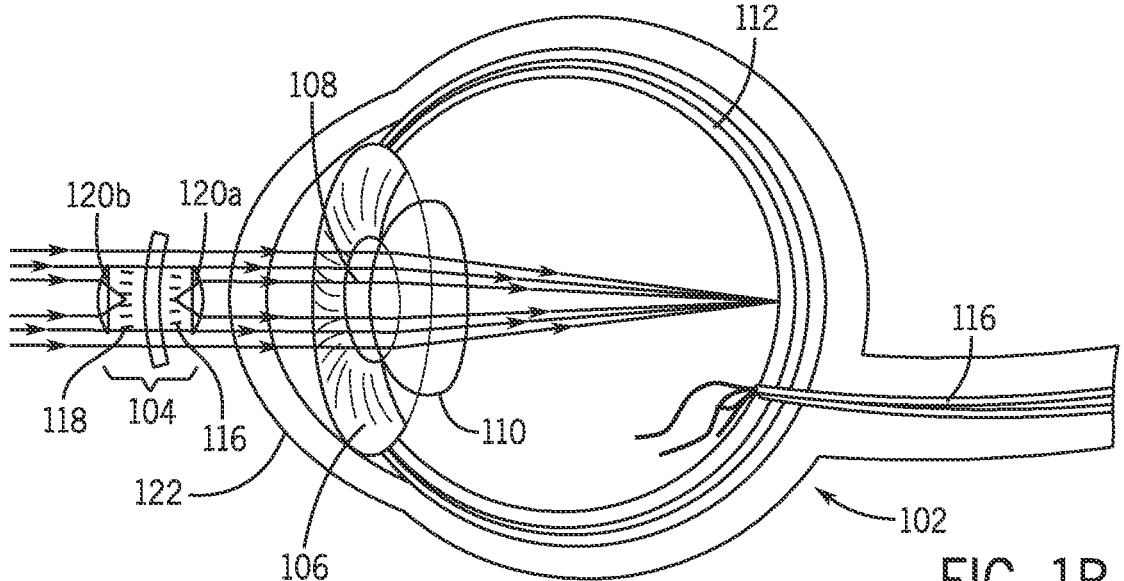
FIG. 1A
FIG. 1B
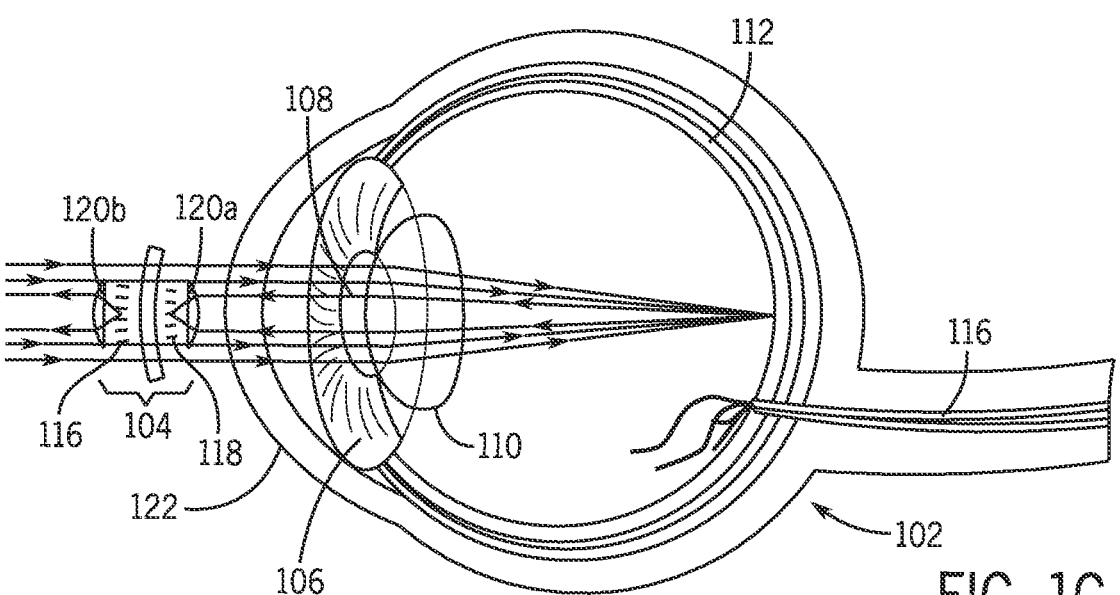
FIG. 1C

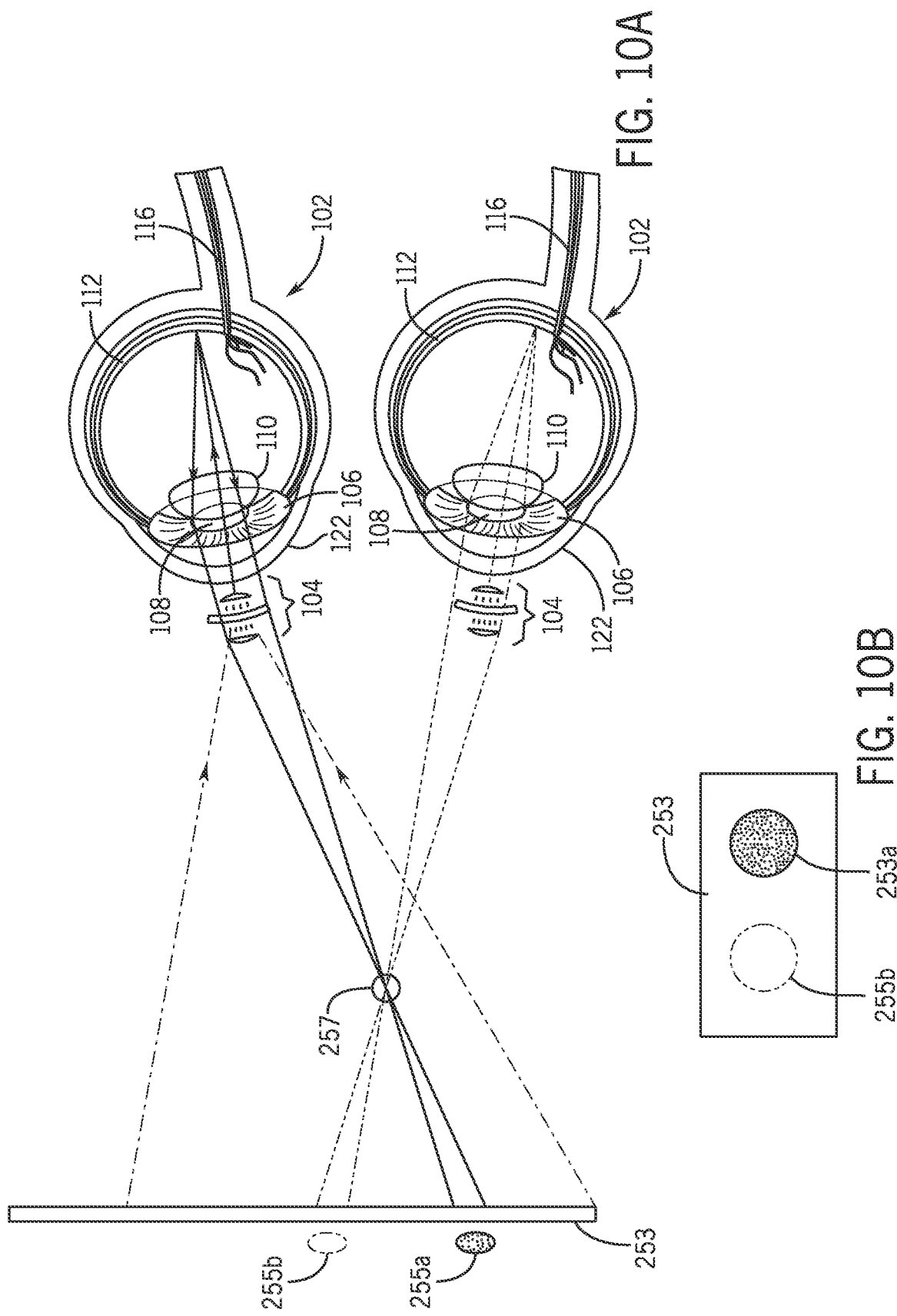

CALIBRATION, CUSTOMIZATION, AND IMPROVED USER EXPERIENCE FOR BIONIC LENSES

CROSS-REFERENCE TO RELATED APPLICATIONS

This is a divisional of U.S. patent application Ser. No. 16/455,012, filed Jun. 27, 2019 and titled "CALIBRATION, CUSTOMIZATION, AND IMPROVED USER EXPERIENCE FOR BIONIC LENSES," which is hereby incorporated herein by reference in its entirety for all purposes.

FIELD

The present disclosure relates generally to bionic contact lenses worn on a user's eye.

BACKGROUND

Bionic contact lenses, such as a smart contact lenses, that are worn or inserted into the eyes of users are quickly developing. Generally, these lenses may include circuitry and sensors that provide or generate information that can be displayed direct into the user's eye. For example, some bionic contact lenses include displays that generate images presented directly into a user's eye. Some bionic lenses also include integrated cameras that capture images from approximately the same viewpoint as the user. Many technology fields, such as alternate reality and virtual reality technologies, are looking to leverage the lenses for new applications and techniques. For example, with AR/VR applications, the display on the bionic lens generates images that can be directly overlaid with the user's "real world" vision, since the image formed by the light from the display is projected, along with light from the world, onto the user's retinas, forming the user's view. However, to operate accurately and provide an immersive user experience, the calibration and accuracy of the bionic lenses is important, current lenses may not be accurately calibrated, hindering the user experience.

Additionally, certain aspects of the lenses can be leveraged to further increase the user immersion, as well as provide important and useful tools for the applications utilizing bionic lenses.

SUMMARY

In one embodiment, a system to calibrate bionic lenses configured to be positioned on the eye of a user is disclosed. The system includes a replica human eye model to receive a bionic lens, the model including an image sensor positioned at a focal length corresponding to an average human focal length, a display that displays a calibration pattern, the display being in optical communication with the image sensor and the bionic lens, and a computer in electrical communication with the images sensor. The image sensor captures at least one calibration image corresponding to the displayed calibration pattern, the at least one calibration image corresponding to the calibration pattern as viewed through the bionic lens and the computer compares the captured at least one calibration image to the calibration pattern as displayed, or fits the captured calibration image to a mathematical model, and determines the characteristics of intrinsic parameters (e.g. focal length, decentering, distortion) of the bionic lens. Alternatively, the rear surface of the model can be a diffuse screen, and an external camera captures an image of the calibration patterns projected through the bionic contact lens and model eye.

In another embodiment, a method to calibration distortion of a bionic lens is disclosed. The method includes displaying by an onboard display of the bionic lens a calibration pattern into an eye of the user wearing the bionic lens; capturing by an image sensor a calibration image corresponding to light exiting the eye generated by the displayed calibration pattern reflecting from a retina of the eye; comparing by the processor the calibration image to the calibration pattern to distortion introduced by the bionic lens and optionally the human or biological lens; and generating by the processor a compensation map for the bionic lens and optionally the human or biological lens to compensate for the distortion.

In one embodiment, a method to determine eye characteristics of a user wearing one or more bionic lenses is disclosed. The method includes capturing by a first bionic lens worn in a first eye of the user a first image corresponding to a calibration pattern positioned at a first orientation of the user relative to the calibration pattern, capturing by the first bionic lens a second image corresponding to the calibration pattern positioned at a second orientation of the user relative to the calibration pattern; and analyzing the first image and the second image by a processor to determine the eye characteristics of the user. This method can be used to determine interpupillary distance, calibrate the onboard camera of the bionic lens, and/or determine pupil swim. It should be noted that in some embodiments, multiple images are captured from various orientations as needed, such as n images may be captured and analyzed.

In another embodiment, a method to determine an interpupillary distance between two eyes is disclosed. The method includes capturing by a bionic lens camera an image corresponding to a reflection of two eyes on a surface, analyzing the image by a processor to detect an iris location for the two eyes; and estimating by the processor the interpupillary distance based on the detected iris location for the two eyes. In one embodiment, the irises are detected and the iris diameter can be used as a reference scale to determine the interpupillary distance.

In yet another embodiment, a system for determining physical characteristics of an object is disclosed. The system includes a contact lens including an image sensor and a processor in communication with the contact lens. The display emits a calibration pattern that reflects on the object, the image sensor captures a calibration image of the calibration pattern as reflected on the object, and the processor compares the calibration pattern to the captured calibration image to analyze distortions of the calibration pattern and determine one or more object characteristics.

In an embodiment, a method to determine a shape of the object is disclosed. The method includes projecting light from a first bionic lens positioned on a first eye of a user onto the object, capturing a first image corresponding to the light projected by the first bionic lens onto the object, capturing a second image corresponding to the light projected by the second bionic lens onto the object, projecting light from an external source positioned on the user onto the object, and analyzing the first image and a first location corresponding to the first eye, the second image and a second location corresponding to the second eye, and a third image and a third location corresponding to the external source to determine the shape of the object.

In another embodiment, a method to determine vergence and focus information for a user is disclosed. The method includes activating a first light display of a first bionic lens positioned on a first eye of the user to emit a first beam of light, activating a second light display of a second bionic lens positioned on a second eye of the user to emit a second beam of light, detecting a first location corresponding to a reflection point of the first beam of light on an object, detecting a second location corresponding to a reflection point of the second beam of light on an object, analyzing the first location and the second location to determine an intersection location of the first beam of light and the second beam of light, and utilizing the intersection location to determine a vergence and focus area of the user.

In one embodiment, a method for converting eye movements of an actor into computer animated movements is disclosed. The method includes activating a first bionic lens worn on a first eye of the actor to emit a first light, activating a second bionic lens worn on a second eye of the actor to emit a second light, tracking movement of the first light and the second light; and converting the tracked movements of the first light and the second light into animated movement of a first character eye and a second character eye, respectively.

In yet another embodiment, a method to generate biometric information for a person is disclosed. The method includes projecting a light pattern by a display positioned on a contact lens into an eye of the person, capturing by an image sensor positioned on the contact lens, a plurality of images of the eye corresponding to a display sequence of the light pattern; generating an eye map (e.g. retinal image) corresponding to the captured plurality of images, wherein the eye map is specific to the eye of the person.

In another embodiment, an interactive environment is disclosed. The environment includes a plurality of smart objects including a camera and a computer in communication with one another and a bionic lens system configured to be worn by a person within the interactive environment, including a first lens having a first display and a second lens having a second display. The first display and the second display emit a first light pattern and a second light pattern and the plurality of smart objects detect the first light pattern or the second light pattern, analyzing the first and second light patterns to generate a customized experience specific to the person.

BRIEF DESCRIPTION OF THE DRAWINGS

FIG. 1A is a front elevation view of a bionic lens system positioned on an eye.

FIG. 1B is an exploded partial cross-section view of the system of FIG. 1A.

FIG. 1C illustrates an implementation of the system where the bionic lens includes a retinal facing image sensor and outward facing projector.

FIG. 10A is a flow chart illustrating a method of determining focus or gaze information via the bionic lens system.

FIG. 10B is a schematic of a system utilizing a first bionic lens and a second bionic lens to determine gaze information of a wearer.

SPECIFICATION

Figure 1D:
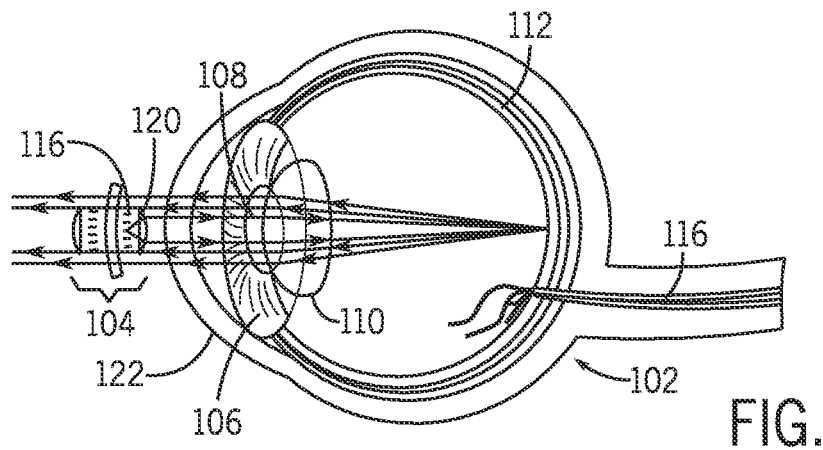
FIG. 1D illustrates an implementation where the bionic lens is used as an in-to-out projection system.

The present disclosure is related to systems and methods for improving functionality, sensitivity, accuracy, and user experience with bionic lenses that are worn or inserted into a user's eye. The techniques described help improve device performance, data capture, and the like. As used herein, the terms "bionic lens" and/or "bionic contact lens" are meant to encompass both lenses that are removably inserted onto a user's eye, as well as those that are implanted or otherwise more permanently connected to a user's eye.

FIG. 1A is a front view of a system 100 including an eye 102 and a bionic lens 104 positioned on the cornea thereof. FIG. 1B is an exploded view of the system 100. In this example, the bionic lens 104 is positioned on an outer surface of a cornea 122 of the eye 102, sufficient to receive and alter light that travels to and from the eye lens 110 and/or retina 112. For ease of explanation, the eye 102 generally includes a cornea 122 that forms an outer surface of the eye 102, the iris 106 is a diaphragm (typically is the colored area of the eye) defining a central opening forming the pupil 108. Behind the iris 106 is the adjustable eye lens 110, which helps to form images on the retina 112 by focusing and collimating light. The retina 112 is formed on an interior of the eye 102 and includes photoreceptor nerve cells, rods, and cones and connects to the optical nerve 116 to send image information to the user's brain. As light enters the eye 102, the iris 106 contracts or expands the pupil 108 to regulate the amount of light reaching the retina 112, then the light passes through the pupil 108 and through the eye or biological lens 110. The cornea 122 and lens 110 focuses the light rays onto the retina 112, which then senses light and generates electrical impulses that are sent through the optic nerve 116 to the brain. In certain instances, light that reaches the retina 112 may scatter and partially reflect off the retina 112 and exit the eye 102 via the eye lens 110.

In one example, the bionic lens 104 is positioned on a user's eye 102 over the cornea. The bionic lens 104 may generally include various electrical components and sensors, depending on the desired functionality and engagement with the user, these components may be positioned onboard a substrate forming the lens (typically transparent), allowing the sensors and electrical components to be directly in contact with the user's eye. In other examples, the bionic lens 104 may be implanted into a user's eye, such as replacing the biological lens 110. In these instances, the bionic lens 104 may be positioned behind the iris 106, rather than in front of the iris 106 on the cornea. As can be appreciated, the variation in the position of the bionic lens 104 likely will change characteristics and positions of the electrical components and sensors. As such, any discussion of a particular implementation is meant as illustrative only and specific examples of positioning, type, size, and functionality for the bionic lens 104 are not meant to be limiting.

Figure 2:
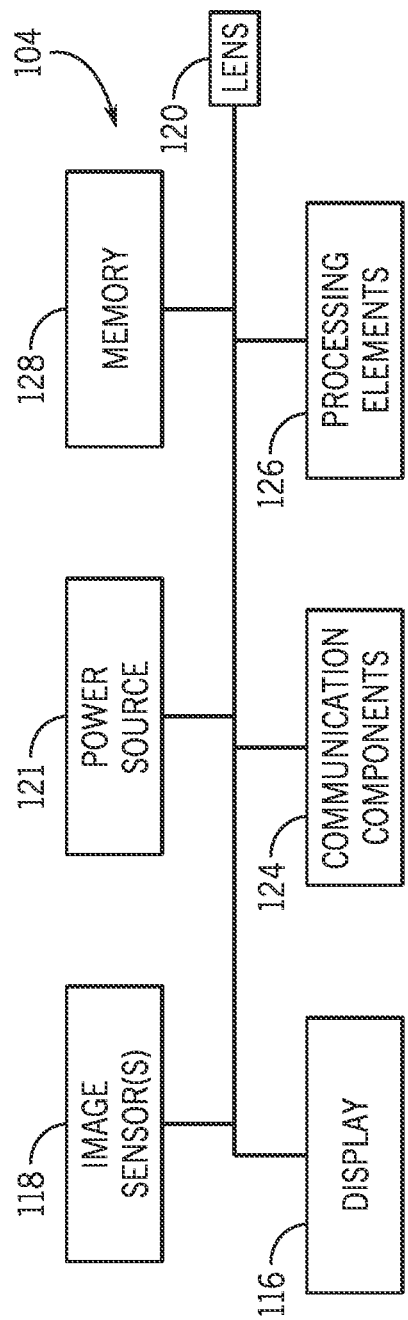
FIG. 2 is a simplified block diagram of the bionic lens system of FIG. 1A.

FIG. 2 illustrates a simplified block diagram of the bionic lens 104. With reference to FIGS. 1B and 2, the bionic lens 104 may include a display 116, an image sensor 118 or camera, one or more optical elements 120 (e.g., lens 120*a*, lens 120*b*), a power source 121, a communication interface 124 or component, a processing element, and/or a memory component 128. The features may be integrated into the bionic lens 104 or certain elements, e.g., power and processing elements, may be in communication with the remaining components, either wirelessly or in a wired manner, that is outside of the worn bionic lens 104. The structure of the bionic lens 104 and its onboard or external components may be varied depending on the uses and functionality, as such, the description of any particular embodiment is meant as illustrative only. Additionally, although only a single bionic lens 104 is shown, it should be appreciated that generally the system 100 may include a bionic lens 104 for each eye 102 (left and right) of the user. In these instances, the two bionic lenses 104 may be the same as one another or may be different, e.g., one may include the image sensor 118 and the other may include the display 116, or the like, to minimize the size requirements for the lenses 104. To that end, many components of the bionic lens 104 may be formed as an integrated circuit and may be transparent where possible, allowing as much light as possible to be transmitted through the bionic lens 104 to the user's eye 102. As an example, in instances where the electronic components are opaque, they may be arranged on the lens 104 in a manner that reduces the occluded area, i.e., have as small of a footprint on the lens 104 as possible, such as arranged around a peripheral edge or clustered together in particular location. The spacing and type of electronic components will also vary based on the uses of the lens 104 and included electronic components.

The image sensor 118 may be substantially any type of device that can capture or sense light, either or both visible and non-visible wavelengths. For example, the image sensor 118 may be a complementary metal oxide semiconductor (CMOS) or charged couple device (CCD) camera. The display 116 may be a microdisplay or other small format display that generates light output or emits light corresponding to electronic inputs, e.g., forms images or patterns. In some instances, the display 116 may also be used as an image sensor, such as by utilizing light sensitive elements, such as light emitting diodes or the like, to generate electrical signals corresponding to the amount of light detected. The type of display 116 will likely depend on the size constraints for the lens 104, but in some instances may be a micro light emitting diode (LED) or organic light emitting diode display. In many embodiments, the display 116 will be oriented to face towards the user's eye 102 when positioned on the cornea. However, in some examples, the display 116 may also include outward facing elements, to generate light that is directed away from the user's eye and/or may include one or more lenses so that the image can be projected from the front of the bionic lens 104 as well and capture images along the user's sight line. The display may be arranged as a projector to project light out of the eye or project light in a manner that is likely to be reflected from the retina and reflect back out of a user's eye. As such, although the term display is used, the functionality may be similar to a projector in some embodiments herein.

The optical component 120, e.g., one or more lenses 120*a*, 120*b*, of the bionic lens 104 is a transmissive structure that focuses or disperses light beams. Generally, the optical component 120 will be a focusing lens that is in optical communication with the eye lens 110 and the display 118 to collimate light from the display 118 such that a relaxed user's lens (focused at infinity) forms a sharp image of both the outside world and off the display 118 onto the retina 112. In some instances, the optical component 120 may be integrated into the display or otherwise work with an integrated display that collimates light onto the biological lens. The type of optical component 120 and shape, e.g., convex, concave, etc., will vary depending on the desired images to be formed on the user's eye and applications. In some instances, the optical element 120 may form a substrate for the remaining components of the bionic lens 104 and may not include any light varying aspects, merely acting as a transparent support for the electrical components of the bionic lens 104.

The power source 122 provides power to the components of the bionic lens 104 and may be a portable or wireless source or a wired variation, e.g., battery, magnetic or inductive coupling, radiative techniques, or the like. The type of power source 122 and the location will depend on the power demands for the lens 104 and can be varied as needed. The communications interface 124 transmits information to and from the bionic lens 104 and between the various components of the lens 104, and may include traced electrical connections, wireless mechanisms (e.g., near field radio transmissions), and so on. The processing element 126 controls the various components of the bionic lens 104 and is any electronic device capable of processing, receiving, and/or transmitting instructions, including one or more graphics processing units, circuits, processors, or the like. The memory 128 stores electronic data used by the processing element 126, image sensor 118, and display 116.

It should be noted that the bionic lens 104 and system can be arranged and function in a variety of different manners, depending on the desired application. FIGS. 1B-1F illustrate various ray diagrams for different use cases for the system 100. Methods and techniques utilizing the various uses shown in FIGS. 1B-1F are described in FIGS. 3A-8C. With reference to FIG. 1B, the light rays illustrates an example of the system 100 where the bionic lens 104 includes an integrated display and an outward facing image sensor 118. In this example, the display 116 emits light towards the user's retina 112 and the image sensor 118 captures light entering the retina 112 (e.g., environmental light). This structure may be used to calibrate the bionic lens, detect gaze of the user, allow three dimensional scanning, as well as other types of applications or uses that require a light projection onto the user's retain, such as alternative reality and scanned camera functionality.

FIG. 1C illustrates another implementation of the system 100 illustrating the directional light rays, where the bionic lens 104 includes an inward or retinal facing image sensor 118 or camera and outward facing projector or display 116. In this example, the onboard image sensor 118 can capture light rays as they appear or form on the retina, including retina images, and the display 116 can project light directly out of the eye, such as onto objects within the environment. This implementation may be used for applications such as wearer identification, health analysis, lens alignment, as well as applications where light is projected outwards, e.g., user interactive games or applications, detection of a wearer's gaze, and three dimensional image mapping via structured light.

FIG. 1D illustrates an implementation of the system 100 where the bionic lens 104 is used as an in-to-out projection system. In other words, the display 116 is oriented so as to direct light inwards towards the retina 112 such that at least some of the light rays will reflect from the retina 112 and travel back through the cornea and out into the environment. This type of light ray reflection and system can be used in applications where it is desirable to project retinal reflected light into the environment, such as for wearer interaction with different objects, detecting gaze, and three dimensional aspects via structured light.

Figure 1E:
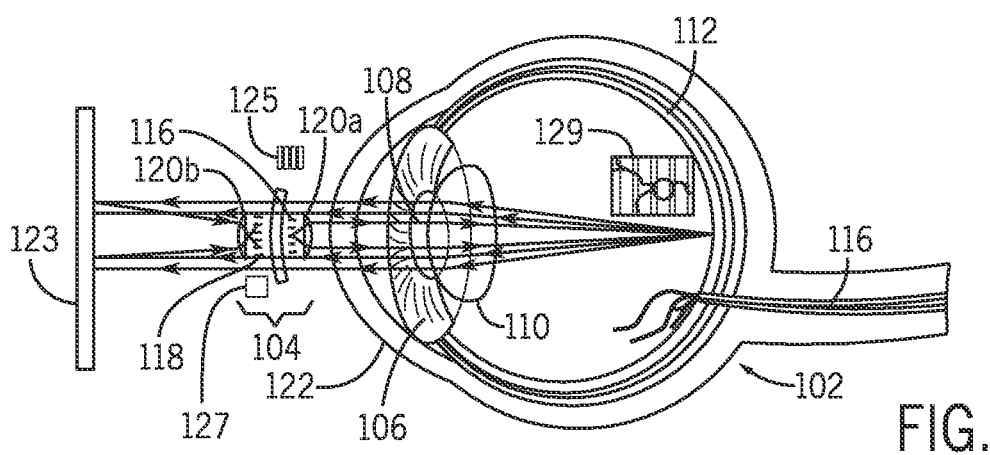
FIG. 1E illustrates an implementation where the bionic lens is used as a retinal scanner.

FIG. 1E illustrates an implementation of the system 100 where the bionic lens 104 can act as a retinal scanner. For example, the display 116 is oriented to direct light, such as a structured light pattern 125 towards the retina 112, then as the light reflects off of the retina 112, the light rays extend out of the eye and onto a reflective surface 123, such as a white board, mirror, or the like, that may scatter the integrated retina pattern back towards the bionic lens 104 so as to be captured by the onboard image sensor 118. In this manner, the image sensor 118 may detect an integrated light pattern 127, which can then be compared to the input structured light projection 125 to generate a retina pattern 129 that is varied based on the biological characteristics of the retina 112.

Figure 1F:
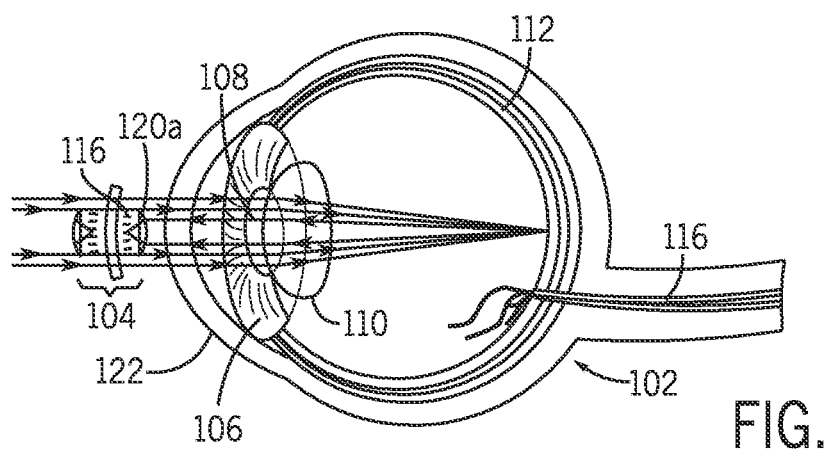
FIG. 1F illustrate an implementation where the bionic lens utilizes the display as a light sensor, capturing light from the environment as reflected from the retina.

FIG. 1F illustrates an implementation of the system 100 where the bionic lens 104 is configured to utilize the display 116 as a light sensor, capturing light from the environment as it is reflected off of the retina 112, e.g., the display 116 may be faced towards the retina 112 but act to detect light as it reflects from the retina 112. This implementation may be used in applications where imaging of the exterior environment as detected by the retina 112 are desired, such as, but not limited to, calibration techniques, gaze detection, and object three dimensional scanning.

Figure 3A:
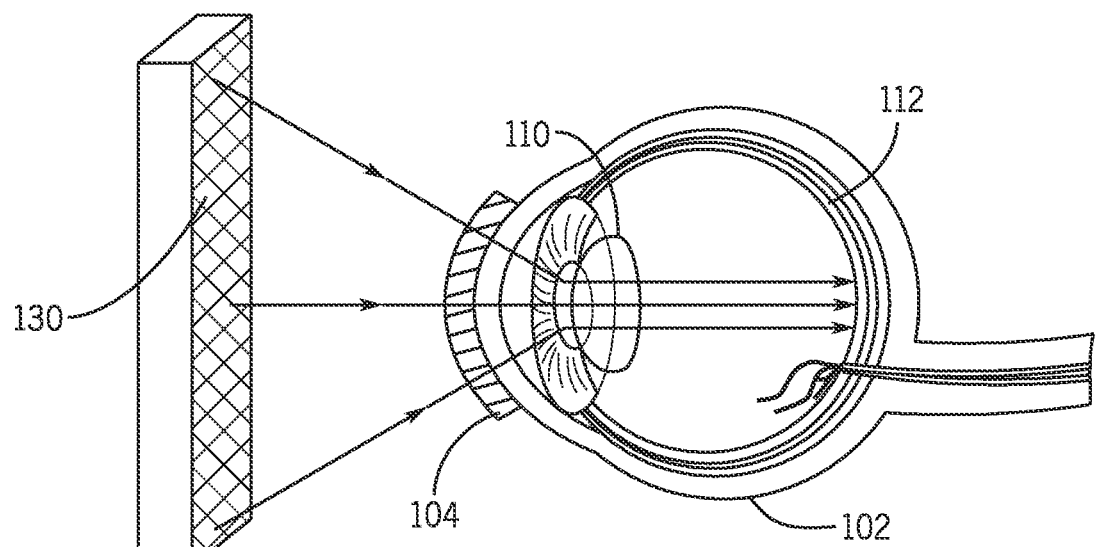
FIG. 3A is a cross-sectional ray diagram of the bionic lens system being utilized as an eye as a camera system.

As shown in FIGS. 1B-1F, the system 100 can be arranged to allow the bionic lens 104 and eye to can function in a few different manners, allowing the user's eyes to essentially act as a camera, act as a projector, and/or a projector-camera system. With reference to FIG. 3A, in this example, the bionic lens 104 includes the image sensor 118 and as the user moves his or her cornea to look at an object 130, the light of the object 130 will reflect from the object 130 and pass through the bionic lens 104 to be captured by the image sensor 118. In this example, the light may be captured by an image sensor positioned on a front or exterior surface of the bionic lens 104 and/or inwards facing display 116 that is leveraged as an image sensor. Continuing with this example, the light beams that reach the eye 102 via the bionic lens 104 can be therefore be captured and in some instances, depending on the diameter and transmissivity of the bionic lens 104, certain rays may reach the user's retina 112 around the lens 104 as well.

As the light rays exit the bionic lens 104, e.g., around the image sensor or through a transmissive image sensor 118, the rays will be focused by the user's eye lens 110 onto the retina 112. These light rays then form the image signals that are transferred to a user's brain, forming the image. Utilizing the captured light rays, the image sensor 118 in the bionic lens 104 will generate an image corresponding to the object 130 viewed by the user. As the user moves his or her eye 102, e.g., to look at different objects, the bionic lens 104 will generally move therewith, allowing the image sensor 118 to capture the various different views and viewpoints of the user. As used herein, the term "eye as a camera" is meant to refer to the concept of utilizing the image sensor 118 in the bionic lens 104 to capture images corresponding to objects and scenes as viewed by the user, such as through the user verging or moving their eyes to look at an object or scene, generally the vergence of the eyes may be correlated to a focus point or location of the user, i.e., where the user is focusing his or her eyes.

Figure 3B:
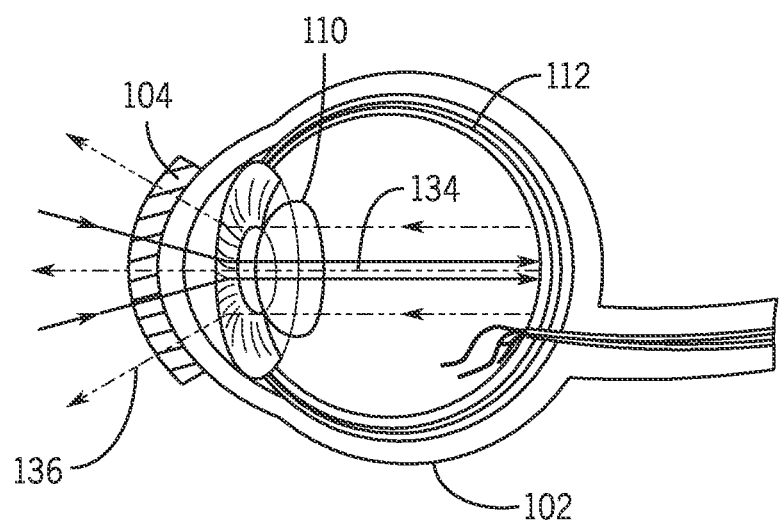
FIG. 3B is a cross-sectional ray diagram of the bionic lens system being utilized as an eye as a projector system.

With reference to FIG. 3B, in this example, the system 100 may be utilized to project light out onto objects. The display 116 generates images that create device rays 134, these rays 134 travel from the display 116, into the user's eye 102 and are focused by the eye lens 110 onto the retina 112. Due to the characteristics of the retina 112, and depending on characteristics of the device rays 134, some light rays may be reflected off of the retina 112 forming retina reflected rays 136. These retina reflected rays 136 may travel from the retina 112 outwards towards the eye lens 110 and through or around the bionic lens 104 towards an external object. As used herein, the term "eye as a projector" is meant to refer to the concept of generating light to be reflected off of the retina 112 and back out through the eye lens 110 to reach the bionic lens 104 and/or be transmitted therethrough or around the lens 104 to the exterior environment. Typically, in these instances, the wavelengths of the projected light may be selected to be in a range that will be highly reflective or scattering from the retina, to allow as much of the projected light as possible to reflect from the retina 112, rather than being absorbed by the retina 112. Also, the light wavelengths may be modulated or otherwise low power to reduce damage to the eye or be uncomfortable for the user. In these instances, the modulated light may be detected via an image sensor or other camera with a demodulation module. Additionally, modulating the light sources may act to increase sensitivity detection in light of lower projection brightness from the bionic lenses and help to reduce noise (e.g., background or ambient light).

Figure 3C:
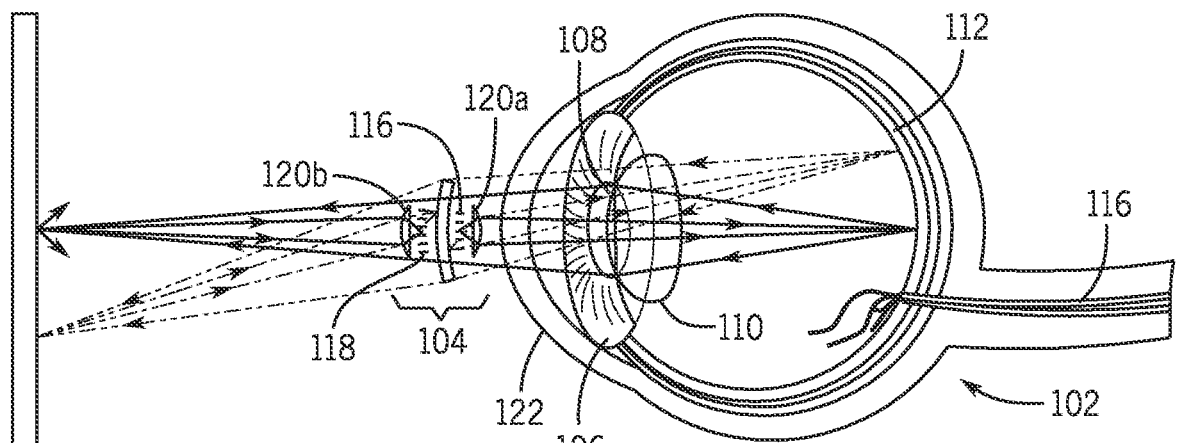
FIG. 3C is a cross-sectional ray diagram of the bionic lens system being utilized as a projector-cam system.

With reference to FIG. 3C, in this example, the system 100 may be used to both project light outwards onto objects in the environment (in-to-out projector) and include an outward facing camera or image sensor 118 that detects light as reflected on environmental objects. This dual directional light is demonstrated by the solid and dashed light rays being generated by the display 116, traveling through the lens 110, reflecting of the retina 112 and traveling out of the eye, and reflecting from an object back towards the bionic lens 104, which can then use the outward facing image sensor 118 to capture images of the reflected light.

Figure 3D:
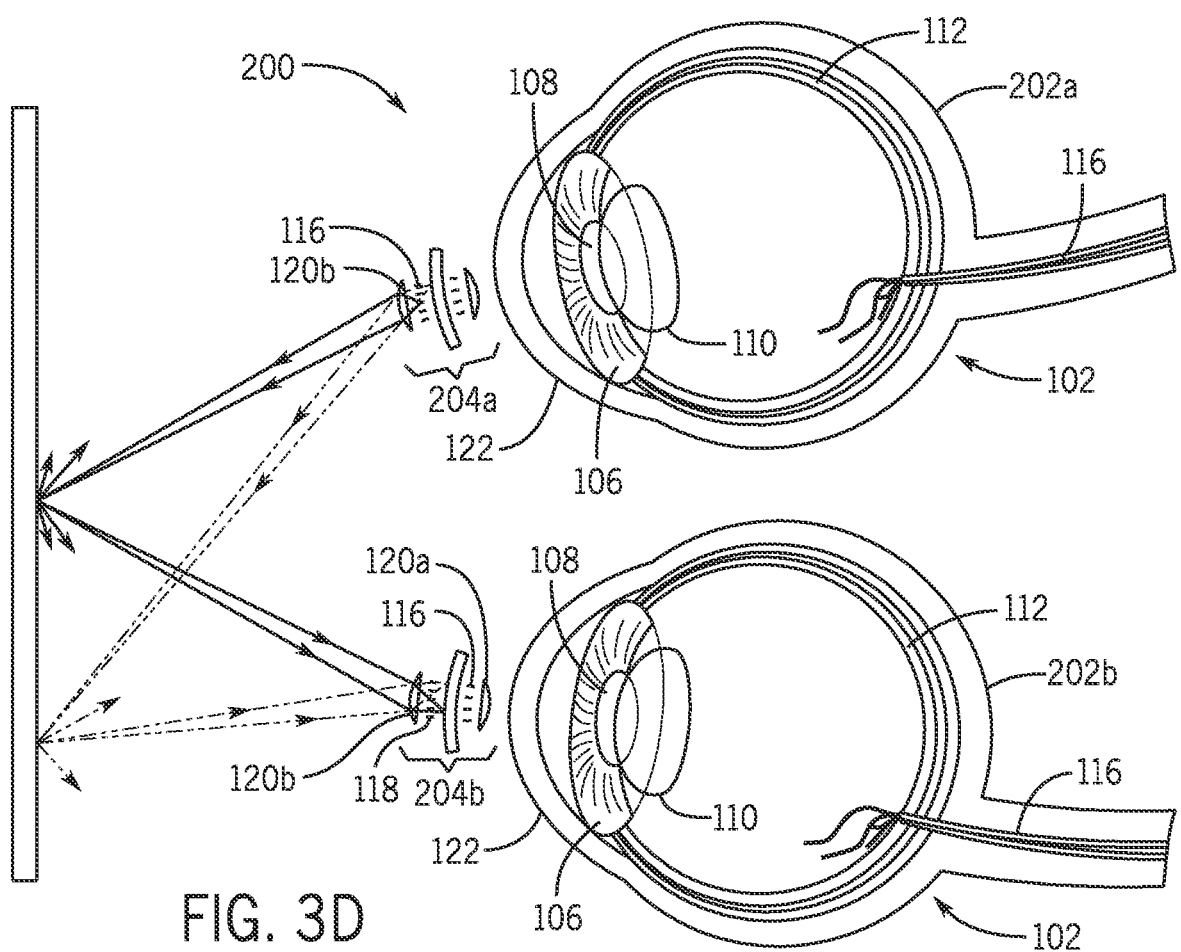
FIG. 3D illustrates a two bionic lens system with a first bionic lens being used as an outward facing camera and a second bionic lens being used as an outward facing projector.

With reference to FIG. 3D, in this example, the system 200 may include two bionic lenses 204a, 204b, the first positioned on a user's first eye 202a (e.g., right eye) and the second positioned on a user's second eye 202b (e.g. left eye). The bionic lenses 204a, 204b may be the same as one another or one may include an outward facing image sensor and the other may include an outward facing display or light projector. In this example, the first lens 204a and eye 202a act as a projector to generate light rays by the display 116 that reflect out of the eye 202a and onto an object and the second lens 204b and eye 204b act as a camera to capture images of the object and the light as projected by the eye as a projector system. As used herein, the term "eye as a projector/camera" is meant to refer to the concept of utilizing the bionic lens 104 to both generate light reflected out of a user's eye and capture light coming into the user's eye, either through two different lenses (as shown in FIG. 3D) or via a single lens system (as shown in FIG. 3C), e.g., the display generates the light and the camera captures the light after it passes from the retina 112 back onto an external object. It should be noted that while the eye as a projector may be executed utilizing two lenses 204a, 204b, in some embodiments, a single bionic lens 104 can both generate the projected light and capture images.

Calibration Techniques

Applications utilizing a bionic lens system 100, such as alternative reality, video gaming, and informational systems, will typically require that the bionic lens 104 has calibrated display and image forming components that account for distortions due to the optical element 120 of the lens (or image sensor 116) and hardware limitations for the display 116, as well as is calibrated to account for variations specific to a user's eye 102, e.g., eye lens 110 optics and the like.

Figure 4A:
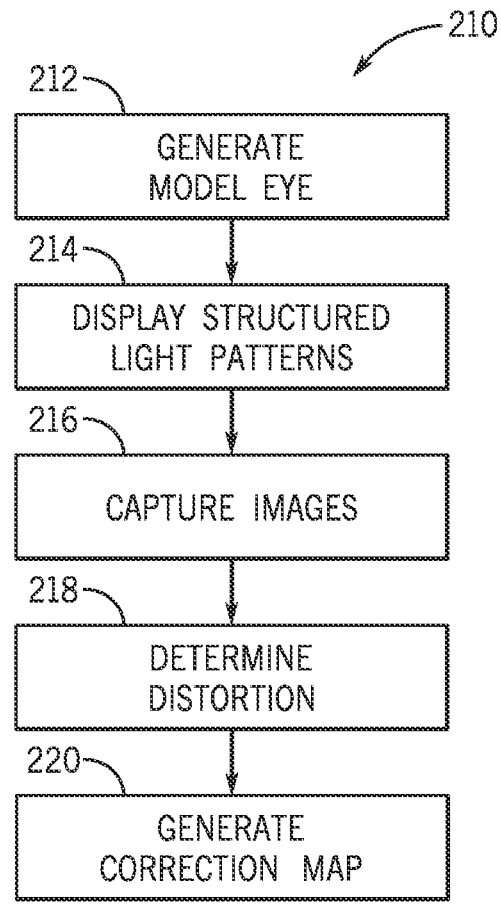
FIG. 4A is a flow chart illustrating a calibration method for the bionic lens system.
Figure 4B:
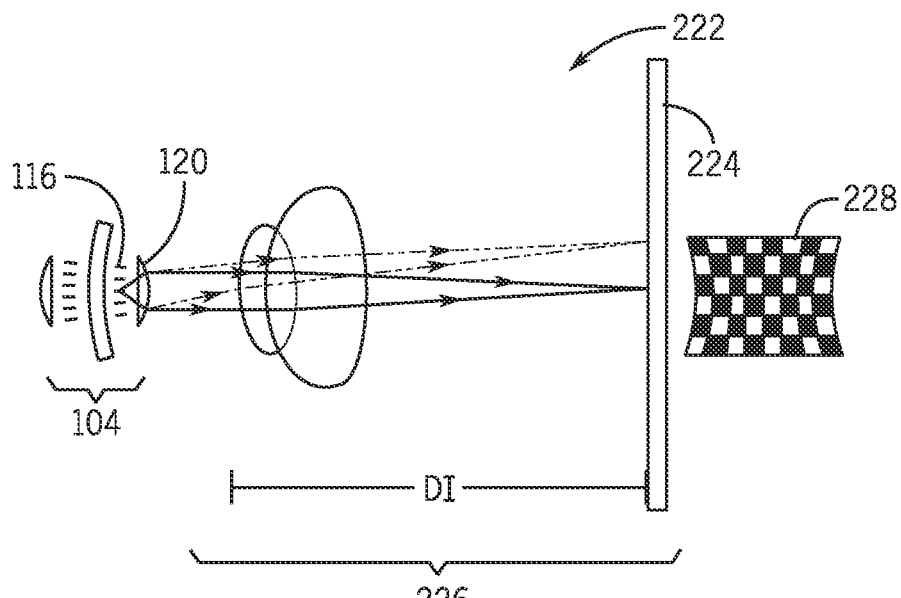
FIG. 4B is an example of a calibration system for the method of FIG. 4A.

FIG. 4A illustrates a method to calibrate the bionic lens 104 to adjust for hardware and optical element 120 or other onboard optical features, such as focusing lenses including on the image sensor or display, that may generate distortions. The method 210 begins with operation 212 and a model eye calibration system is generated. An example of the model eye calibration system 222 is shown in FIG. 4B, which includes an artificial replica of a human eye 226 that may be a single lens (or multiple lenses and apertures) selected to have an effective focal length (D1) of a standard human eye, e.g., around 17 millimeters, as well as a sensor 224 or screen at a back area thereof and optionally a display that can generate images. The calibration system 222 is configured to be able to receive the bionic lens 104, connected in the same manner as it would be worn on a user, e.g., on the outer surface of the eye replica 226. Utilizing the model eye system 222, the method 210 proceeds to operation 214 and structured light patterns or other calibration patterns are projected, either by the display 116 of the bionic lens or by a calibration display integrated into the calibration system 222 or in optical communication with the system 222, e.g., that is able to be captured by the image sensor 224 and the lens 104.

As the images are displayed, the method 210 proceeds to operation 216 and calibration images are captured either by the image sensor 224 or the calibration system 222 or directly by the onboard image sensor 118 of the bionic lens 104. In embodiments where the images are captured by the calibration system 222 image sensor 224, the sensor 224 is positioned so as to replicate the focal length and field of view of the human eye to view the images through the bionic lens 104 as they would appear to a human user, i.e., as would be formed on the retina of the user. It should be noted that the captured calibration images are captured as viewed through the bionic lens 104 and thus through the optical element 120 (e.g., lens material) of the lens itself. The number of calibration images may be varied as needed depending on the type of calibration and sensitivity for the bionic lens.

Once the calibration images are captured, the method 210 proceeds to operation 218 and a processing element or computer determines the intrinsic parameters of the bionic lens 104, such as focal length, lens to center characteristics, distortion parameters including the distortion introduced by the optical element 120 of the bionic lens 104. For example, the computer can compare the known characteristics of the calibration patterns or structured light patterns (e.g., pattern 228) as displayed (e.g., original or input images) to the light pattern images as captured by the model image sensor 224. Differences between the captured light patterns and the displayed patterns reflect the distortion introduced by the optical element 120 of the bionic lens 104. For example, as shown in FIG. 4B, the calibration pattern 228 as captured by the image sensor 224 is shown distorted in shape, rather than a rectangular shape of the input calibration pattern. The distortion characteristics introduced at various locations of the bionic lens 104 can be stored as a mapping, lookup table, or other relational structure. In some embodiments, the distortion characteristics can be compared against a threshold to determine if the lens quality meets a particular standard, e.g., manufacturing or factory standards.

In some instances, utilizing the determined distortion characteristics, the method 210 proceeds to operation 220 and a lens correction map is generated. For example, the computer can generate a calibration map or other algorithmic relationship that can be applied to input images to be formed on the onboard display 116, that will counteract the distortion introduced by the optical element 120, ensuring that the user will see the desired displayed images (rather than distorted images). Utilizing the calibration system 220, manufactures can help to ensure quality and standardized products.

Figure 5A:
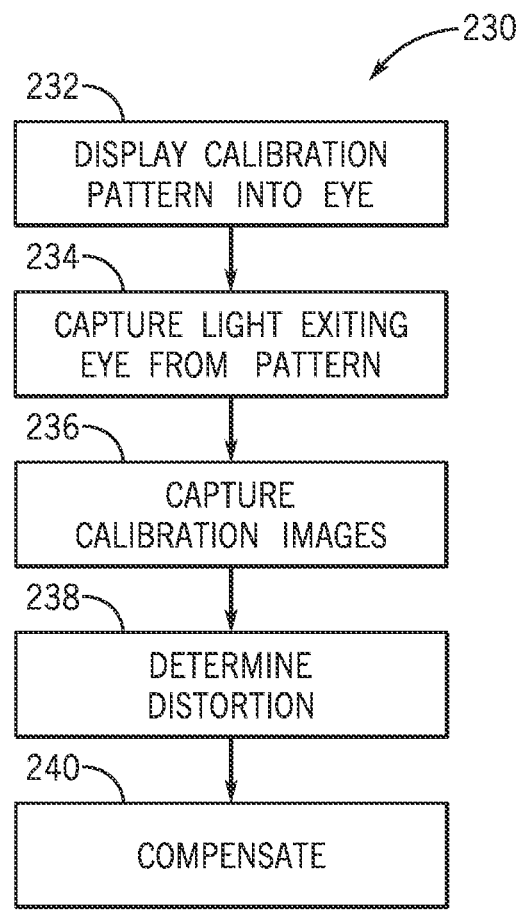
FIG. 5A is a flow chart illustrating a method to determine and compensate for distortion in the bionic lens system.
Figure 5B:
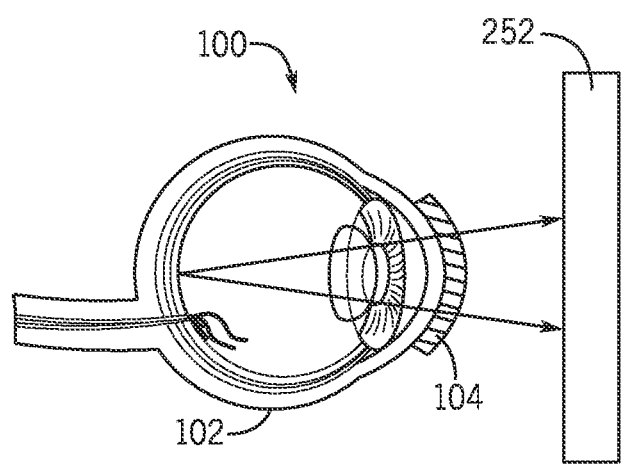
FIG. 5B is a top cross-sectional view of the bionic lenses as one example of the method of FIG. 5A.

With reference to FIG. 5A, in some instances the calibration for the bionic lens 104 may also take into account distortions introduced by the biological eye lens 110. For example, when utilizing the eye as a projector, distortions in the light exiting the user's eye 102 (e.g., due to the user's biological eye lens 110) may be determined and compensated. In one example, the calibration method 230 includes operation 232 and one or more calibration patterns (e.g., structured light) are displayed by the display 116 of the bionic lens 104 into the user's eye 102. As described with respect to FIG. 3B, as the light rays from the display 116 scatter or reflect from the retina 112, the light rays will pass back through the user's eye lens 110 and bionic lens 104 to an external object.

As the calibration patterns are displayed and directed out of the user's eye 102, the method 230 includes capturing calibration images of the light patterns after they have exited the eye 102. In one embodiment, shown in FIG. 5B, the exiting light patterns may be captured directly via an external calibration sensor 252. In this example, the calibration sensor 252 is positioned in front of the user's eye 102 and configured to capture all light rays at all angles as they exit the bionic lens 104 and the eye 102. In some instances, the camera 252 has a sufficiently large lens and is focused at infinity in order to ensure that all the light rays exiting are captured. The light patterns may also be modulated, so that low power illumination can be used, as not to damage the user's retina, but still allowing the modulated light to be detected by an appropriate sensor/camera with demodulation circuitry.

Figure 5C:
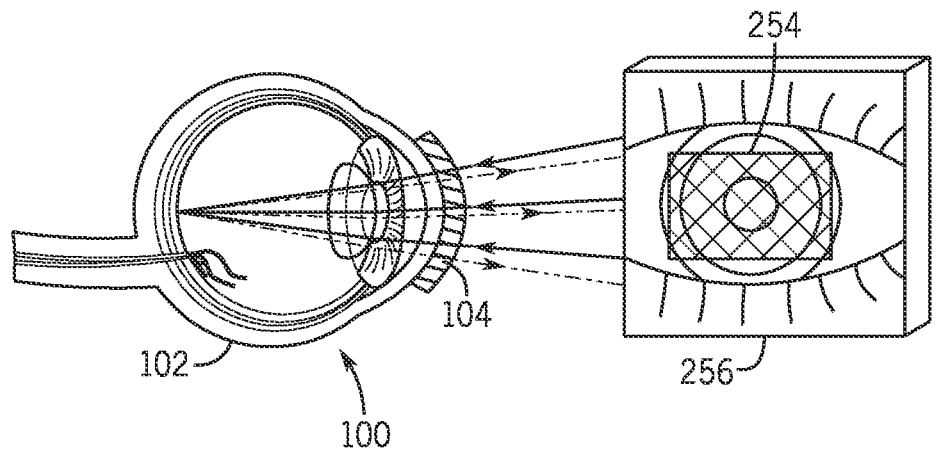
FIG. 5C is a perspective cross-sectional view of the bionic lenses as another example of the method of FIG. 5A.

In another embodiment, shown in FIG. 5C, the onboard image sensor 118 can be used to capture the light rays. In this embodiment, the user is positioned in front of a mirror 256 or other reflective or retroreflective surface and as the light rays generated by the calibration pattern as formed on the retina 112 exit the eye 102 and bionic lens 104, they are collimated by both the user lens 110 and optionally the optical element 120 within the bionic lens 104, and then reflected back towards the bionic lens 104 from the surface of the retroreflector 256. As shown in FIG. 5C, the calibration distorted pattern 254 as formed on the retina and collimated by the lenses is visible within the retroreflector 256. The bionic lens 104, via the onboard image sensor 118, then captures an image of the reflection, including the distorted calibration pattern 254.

With reference again to FIG. 5A, after the calibration images of the distorted calibration pattern exiting the eye are captured in operation 236, the method 230 proceeds to operation 238 and a processing element or computer determines the distortion. For example, the input calibration patterns as displayed by the display 116 into the user's eye 102 are compared to the captured distorted patterns and the variations between the two images can be used to determine a distortion mapping describing the distortion imparted by the system 100, e.g., the biological lens 110 and the bionic lens 104. Utilizing the distortion, the method 230 can then proceed to operation 240 and the system 100 can compensate for the distortion, such as by generating a distortion map that is applied to input images to be displayed by the onboard display 116, such that the images will be corrected to compensate for the system distortion.

It should be noted that in some embodiments, the calibration method 230 may be performed utilizing non-visible light, such as infrared light or other light wavelengths that may scatter less on a user's retina 112, to allow more accurate calibration.

Figure 5D:
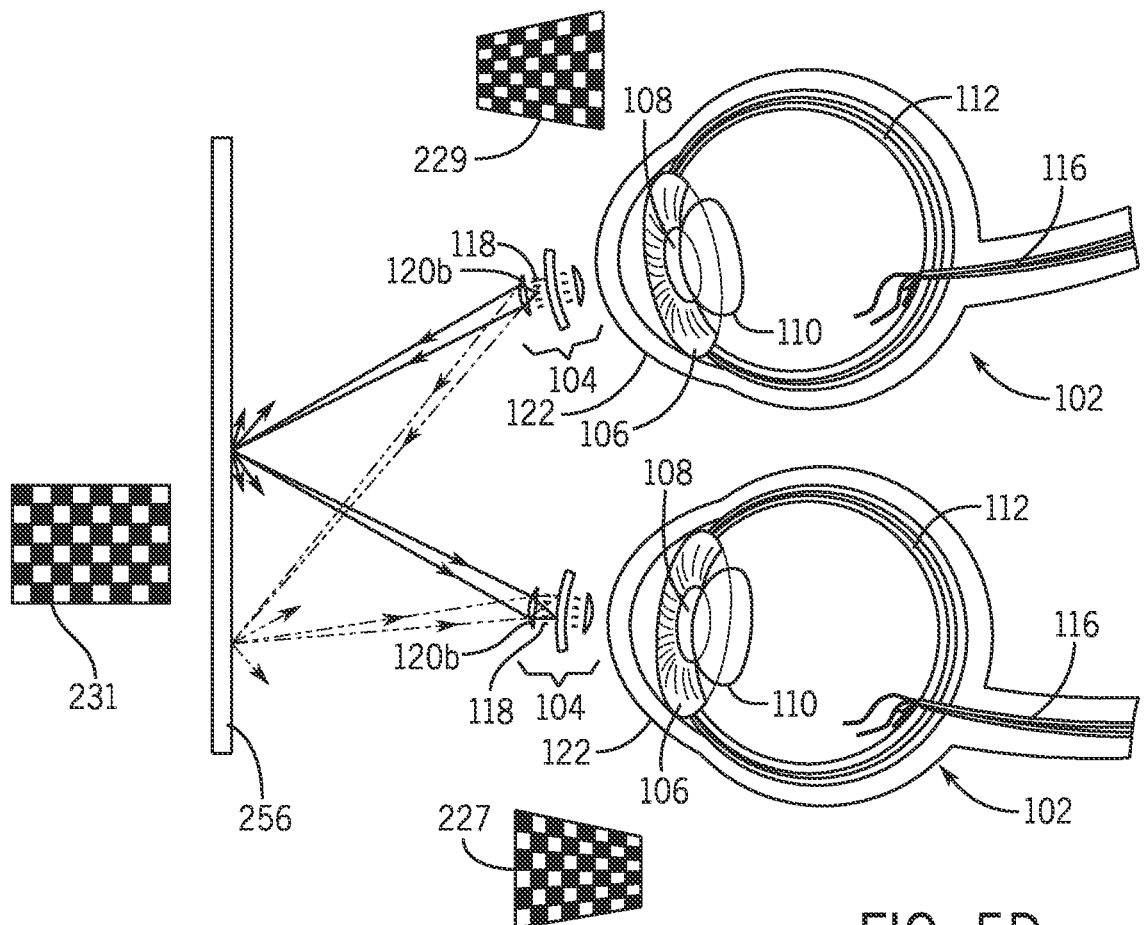
FIG. 5D is a top schematic view of two bionic lenses being used during a calibration process.
Figure 5E:
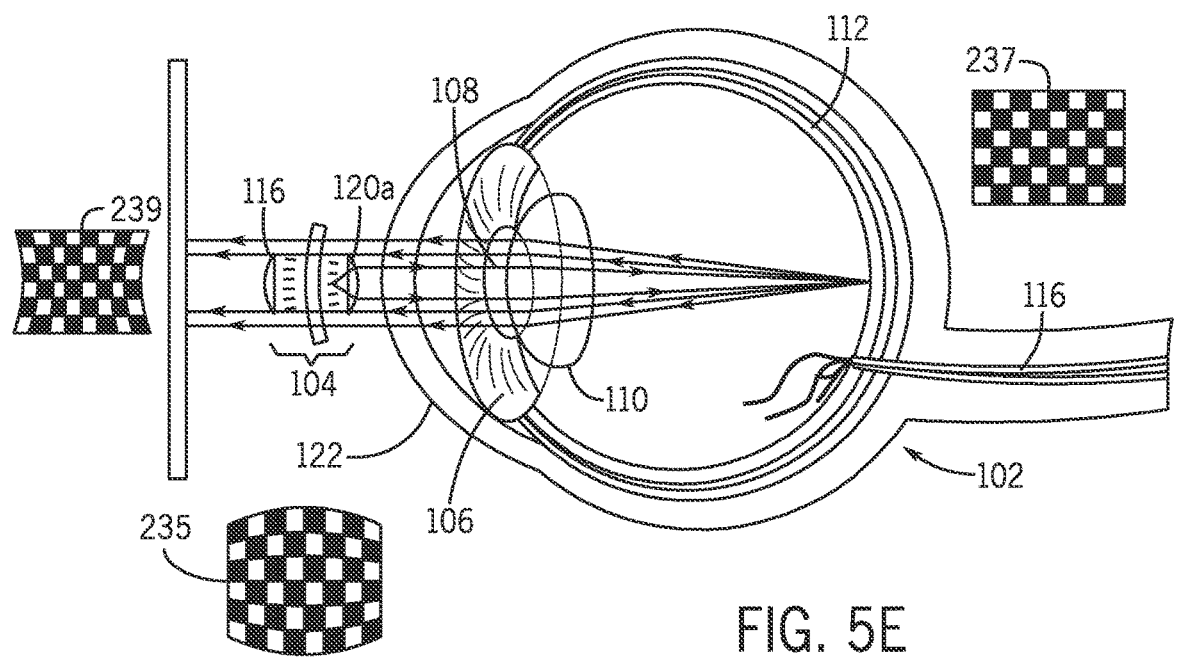
FIG. 5E illustrates an example of a bionic lens being used as an in-to-out projector during a calibration process.
Figure 5F:
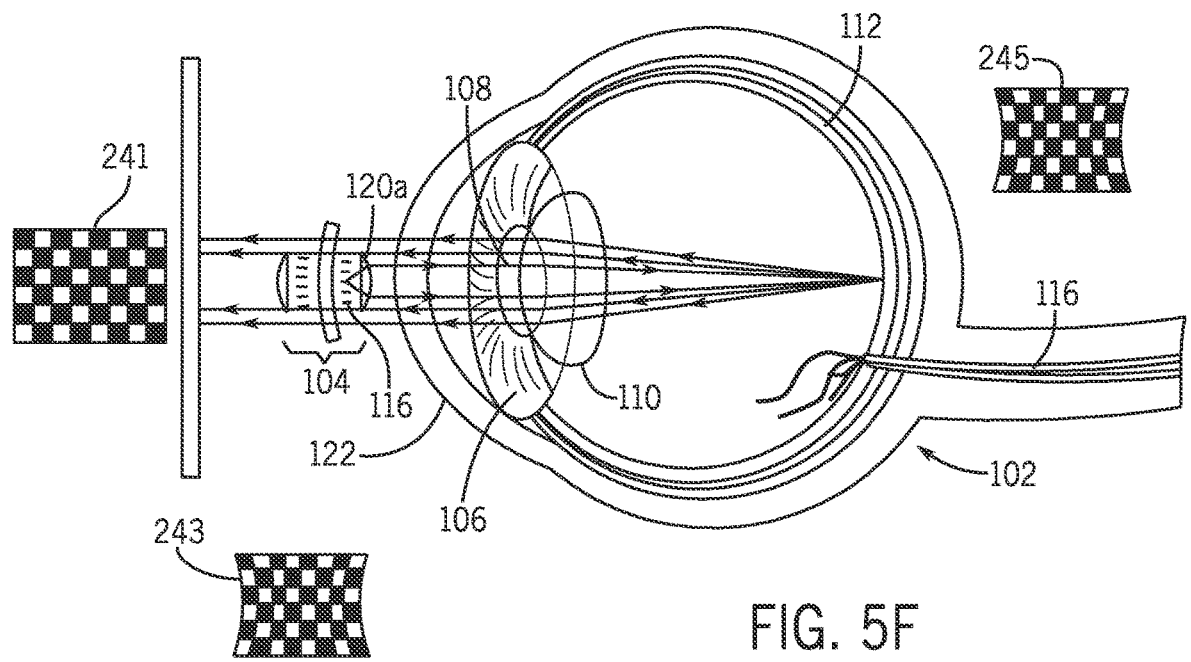
FIG. 5F illustrates an example of a bionic lens being used as an out-to-in camera with the display being used as a light sensor during a calibration process.

FIGS. 5D-FIG. 5F illustrate other calibration examples where the In another embodiment, as shown in FIG. 5F, the onboard image sensor 118 of the bionic lens 104 can be used to capture and image the light rays. In these examples, light rays generated by the calibration pattern are focused by the biological lens 110 to form an image on the retina 112. This image scatters off the retina 112 and is collected by both the biologic lens 110 and the bionic lens 104 to form an image on the display 116, which in some instances is an LED array. As can be appreciated, in LEDs, even those in a display, can act as light sensors, allowing the display 116 to detect light values and act as a light sensor array to capture the image of the calibration pattern that passes through both the user's biologic lens 110 and bionic lens 104. From images of the calibration patterns, the intrinsic parameters of the user's lens 110 and the bionic lens 104 can be determined.

With reference to FIG. 5D, the system 100 is arranged as a projector-camera system in order to calibrate the bionic lenses 104 and/or the combination of the biological lens 110 and the bionic lens 104, i.e., compensate for distortion due to the optical elements 120 of the bionic lens 104, the display 116, or the like, and the biological distortions of the wearer's lens 110. In this example, a first calibration pattern 227 is projected by the first bionic lens 104, a projected calibration pattern 231 is formed on the projection surface 256, which may be a reflective surface, such as a retroreflector or mirror, and the second bionic lens 104 captures a calibration image 229 corresponding to the formed calibration pattern 231. In this example, the first lens 104 projects the image and the second lens 104 captures the image, but in other examples, both lenses may project and capture images. In this example, the captured calibration pattern image is compared to the first projected calibration image and used to determine and correct for distortions within the system.

FIG. 5E illustrates a system utilizing the eye as a projector to calibrate or correct for distortions in the bionic lens 104 and/or biological lens 110. In this example, the display 116 projects a first calibration pattern 235 directly onto the retina 112, i.e., inwards facing versus projecting out onto a projection surface. A calibration pattern image 237 is formed on the retina 112 as the light reflects from the retina 112 and then as shown in the ray diagrams, reflects back out through the eye, including through both the bionic lens 104 and biological lens 110. The reflected calibration pattern 239 is then formed on a projection surface and now includes distortions added by the travel through the lenses 104, 110. In one embodiment, the projection surface 239 includes a separate image sensor, which then captures an image of the pattern 239 as it is formed on the surface. As noted above, the light used to form the calibration pattern projected onto the retina 112 may be modulated or otherwise selected to reduce power and ensure no damage to biological tissue.

With reference to FIG. 5F, this system may be similar to FIG. 5E, but the onboard image sensor of the bionic lens 104 is used to captured an image of the distorted calibration pattern 243. Specifically, the display 116 of the bionic lens 104 generates a light pattern corresponding to an input calibration pattern 241. The input calibration pattern 241 is projected towards the retina 112, and a reflected calibration pattern 245 is formed. As shown by the light directional arrows, the image of the reflected calibration pattern 245 then travels back through the biological lens 110 and bionic lens 104, the display 116 acting as an image sensor or the onboard image sensor 118 then captures a calibration image 243 of the distorted pattern. The captured distorted calibration image 243 can then be compared to the input calibration image 241 to determine and correct for distortions caused by the biological and bionic lenses 110, 104.

Determining Eye and Positional Characteristics

Figure 6:
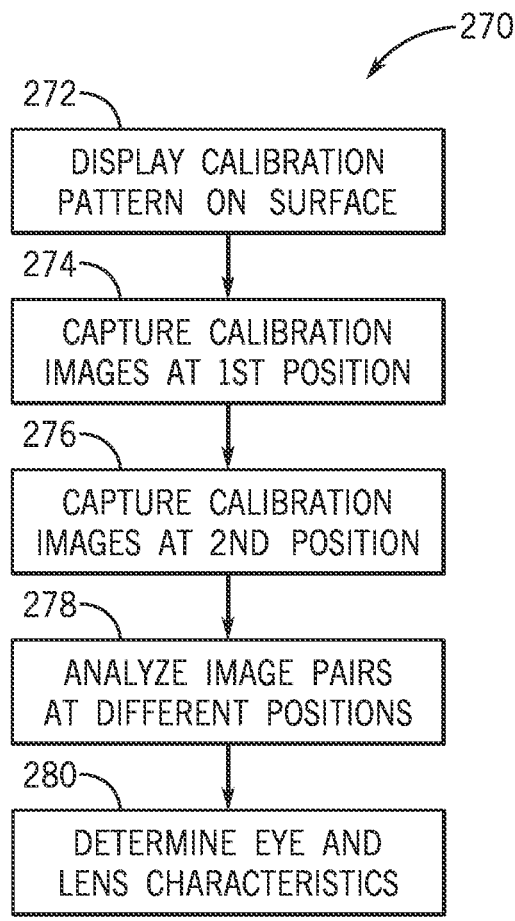
FIG. 6 is a flow chart illustrating a method to utilize the bionic lens system to determine eye and lens characteristics.

In another example, the system 100 can be calibrated to more accurately determine characteristics of the user's eye spacing and body spacing, which is helpful in generating display images that are viewpoint based, require stereo information, or otherwise include positional information, e.g., alternative reality, virtual reality, and depth overlays. FIG. 6 illustrates a method 270 to determine various orientation characteristics utilizing the eye as a camera and/or eye as a pro-cam systems. The method 270 begins with operation 272 and a calibration pattern or reference pattern is displayed on a surface, such as a checkerboard or other structured light pattern. For example, a calibration pattern may be displayed on an external display, such as a computer screen, television screen, or may be a statically formed image (e.g., poster board). In another example, the calibration pattern may be displayed by the system 100 itself, e.g., by the onboard display 116 and relying on the reflection of light back out of the eye 102.

As the calibration pattern is displayed on a surface, one or more calibration images are captured by the image sensor 118 while the user's eye 102 in at a first position. For example, while the user is standing directly in front of the calibration pattern or is looking at the calibration pattern from a first angle or other first location. The method 270 then proceeds to operation 276 and a second set of calibration images or image is captured by the image sensor 116 at a second position, e.g., as the user is standing at a second location relative to the calibration pattern, looking at the calibration pattern from a different angle (moving his or her head or eyes), etc. In some instances, the position of the calibration pattern may be varied, rather than the user. For example, if a television screen is used, the calibration pattern can be projected at different areas on the screen (e.g., upper right hand corner and then the lower left hand corner) or otherwise varied to allow calibration images to be captured at different positions.

Operations 274 and 276 may be repeated any number of times as needed, depending on the desired calibration and orientation information needed, e.g., N number of images may be captured at N number of orientations. In some instances, calibration images may be captured at three or more different positions to provide additional information that can be used in the calibration and orientation process. Additionally, in many cases, the method 270 may include capturing two images for each position, such as from the left and right bionic lenses 104 as the user looks at the calibration pattern.

Utilizing the calibration images at the discrete positions, the method 270 may proceed to operation 278 and a computing device, such as one or more processors, analyzes the captured images, along with the characteristics of the calibration pattern (e.g., pattern size and features, projected or displayed location, etc.). Generally, the analysis will compare the input or known calibration characteristics to the characteristics of the captured calibration pattern to determine differences, such as the translations, rotations, and other extrinsic characteristics of the images. For example, computer vision algorithms used to calibrate stereo camera pairs can be applied to the captured images, and the intrinsic and extrinsic properties (poser, or locations and rotations of the cameras where each picture was captured from) can be determined. Utilizing these parameters and a model of a human interpupillary distance (or known distance), fixed separation distance of the lens image sensors that are rotating behind their points of projection, the interpupillary distance and eye rotational axes can be determined.

With the analysis, the method 270 proceeds to operation 280 and the eye and lens characteristics for the system 100 can be determined. For example, the distance between the images sensors 118 in each of the bionic lenses 104 worn by the user (e.g., left eye lens and right eye lens) can be determined, which may be correlated to the distance between the user's eyes. Additionally, in instances where the calibration positions are varied by a user looking up, down, right and left, the changes in perspective in the calibration images can be used to determine the pupil rotational characteristics, e.g., pivot point or rotational axis relative to the eyeball and center of rotation for the eye. This information is useful to update images that are displayed via the lens 104 to the user that include elements that are varied based on the perspective. Similarly, the analysis can be used to determine the center of rotation of the user's head as well, given that the spacing between the eyes can be determined and by comparing multiple images captured as the user moved his or her head into different positions.

Figure 7A:
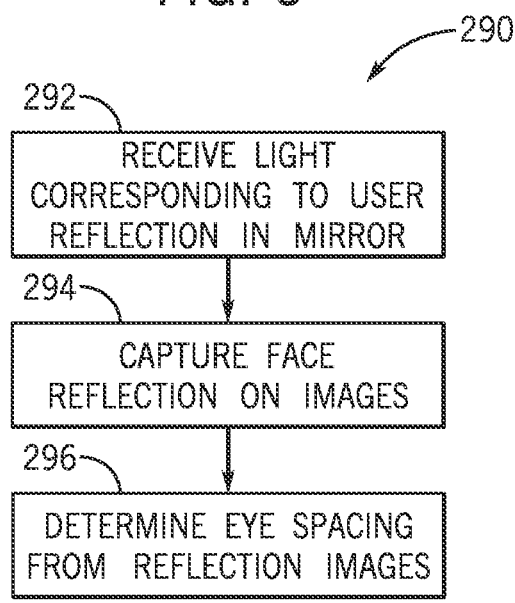
FIG. 7A is a flow chart illustrating a method to utilize the bionic lens system to determine an interpupillary distance of two eyes.
Figure 7B:
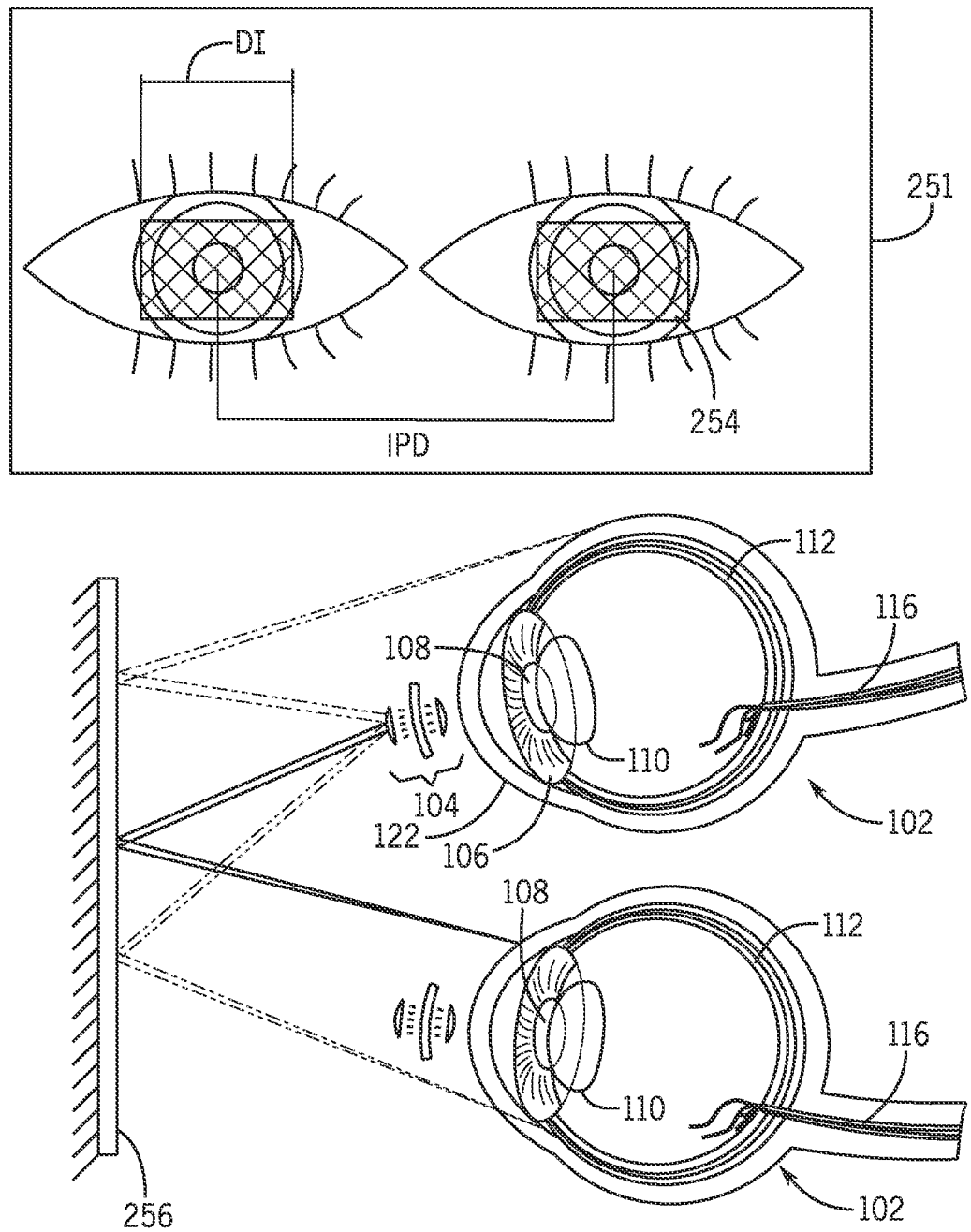
FIG. 7B illustrates a schematic of a system utilizing two bionic lenses to determine an interpupillary distance of two eyes.

Similarly, another method for determining interpupillary distance and eye measurements is shown in FIG. 7A and a schematic of the system is shown in FIG. 7B. With reference to FIG. 7, the method 290 may begin with operation 292 and the image sensors 118 of the bionic lenses 104 may receive light corresponding to user reflection, e.g., light as reflected from a retroreflective surface 256 or a mirrored surface that corresponds to the user. In some instances, the user can follow instructions (e.g., via an application, displayed via the onboard display 116 or the like), that directs the user to stand in front a mirror or other reflective surface 256, allowing the lenses 104 to capture images of the user's face. The method 290 includes capturing one or more facial reflection images by the image sensor 118, the facial reflection images including at least the user's left and right eyes 102.

Utilizing the captured eye images, the method 290 proceeds to operation 296 and a processor or computing element analyzes the captured eye image to determine eye spacing characteristics, such as the inter-pupillary distance. As an example, the processing element may analyze the captured image 251 and using the detected irises and an estimated D1 distance (e.g., a typical diameter for iris, e.g., between 10.2 to 13 mm, with an average size of 12 mm), and then use photogrammetry or other measurement techniques to determine the distance between the two pupils within the captured image 251. Using an image detection algorithm, the location of the irises on in the eye image can be determined (such as by using color detection, subtracting the white of the corner from the colored portions of the iris), and then applying an average diameter of the iris, the processor can extrapolate the distance between the two pupils of the user's eyes using photogrammetry and other image analysis techniques.

Determining External 3D Information

The system 100 can be used to provide information to the user and programs including the bionic lens 104 functionality regarding the shape and characteristics of objects surrounding the user, e.g., the environment. This information can be helpful to further tailor images that will be displayed by the display 116 to the user to conform to the detected shape of the object, providing a more realistic appearance in the virtual space or the like.

Figure 8A:
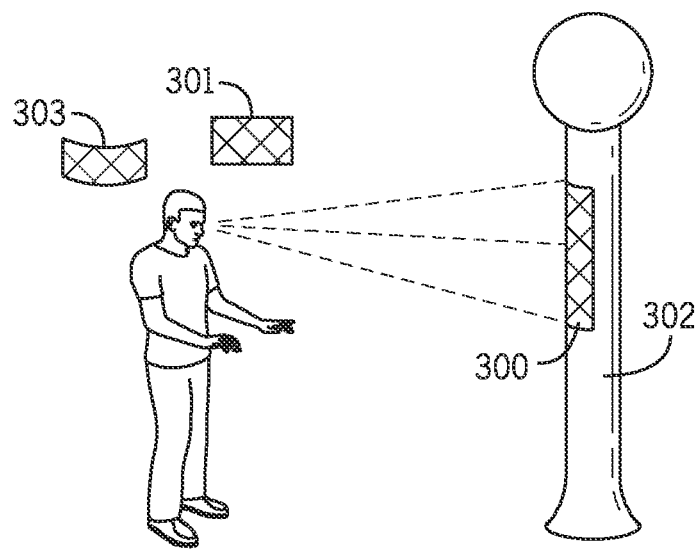
FIG. 8A is an example of utilizing the bionic lens system to determine object characteristics.
Figure 8B:
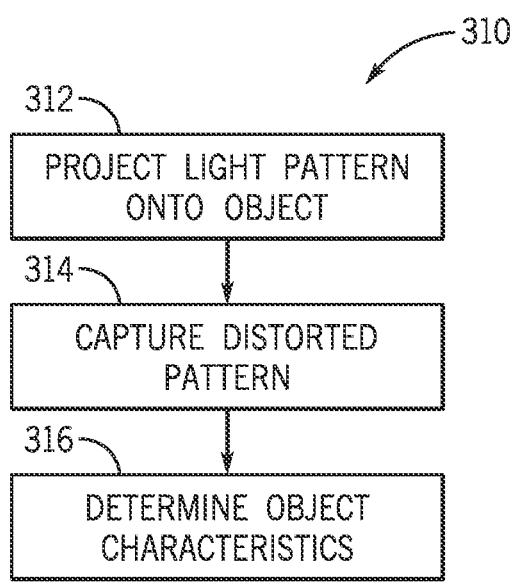
FIG. 8B is a flow chart illustrating a method of utilizing the bionic lens system to determine object characteristics.

One method for determining object shapes and topography is shown in FIGS. 8A and 8B. In this example, the method 310 begins with the lens 104 projecting an input structured light pattern 301 onto an object 302. This may be done via the indirect or reflected light from the display 116 or from an outward facing display and lens (outward facing projector) that directly emits light outwards away from the user's retina 112. In some embodiments, the display may be positioned in front of the bionic lens 104 relative to the retina, such that the light may not travel through the bionic lens 104 before reaching the object. As shown, the projected light pattern 301 is projected onto an object 302, forming a distorted pattern 300 as the light pattern varies to conform to the shape of the object 302.

The method 310 then includes capturing one or more images by the image sensor 118 of the projected light pattern 300. In one example, the image sensor 118 of the non-projecting lens 104 in a projector-camera system captures the images while the lens 104 in the other eye projects the light pattern. In another example, the same lens that is projecting the light may also act to capture images of the projected light on the object 302. The captured images of the distorted light pattern are then analyzed by a computer or processor in operation 316. In this operation, the object topography can be determined by analyzing changes between the input light pattern and the distorted light pattern 300 as projected onto the object 302, e.g., changes in dots or other pattern elements as they interact with the object surface, e.g., a planar surface may not introduce many changes in the shape of the pattern, whereas a curved surface may introduce a particular distortion that corresponds to or is complementary to the shape of the object 302.

It should be noted that the method 310 can be done utilizing both lenses 104, one projecting and one capturing images, a single lens that both projects and captures images, or via a dual projecting/capturing system where both lenses project light patterns and both capture images of the projected light patterns. With this last example, the light patterns emitted from the two lenses 104 may be modulated or otherwise tailored to be identifiable as corresponding to the particular lens (e.g., by color, pattern element shape, projection rate, size, or the like). In this example, two separate patterns from slightly offset locations can be used with known distance relationships between the origination source to provide further data to assist in determining environmental characteristics and topography. Specifically, utilizing photogrammetry algorithms and identifiable correspondences between the images captured by the two offset lenses 104 (e.g., right eye and left eye), known or estimated interpupillary distance or distance between the two lenses 104, a head orientation of the user, position of a user within an environment, object shapes and positions relative to the user can be determined.

Utilizing the projected light, captured distorted images, and the like, the lenses 104 can be used assist in the computation of simultaneous localization and mapping (SLAM) that generates/updates a map of an unknown environment while simultaneously determining and tracking the position of the user or the lenses 104 within the environment. In some embodiments, the bionic lens may include a depth sensing camera that utilizes techniques, such as time of flight or the like, to determine depth characteristics of the object and/or stereogrammetery techniques as well. These techniques can then be used to render viewpoint adjusted content based on the orientation of the user's head and/or a physical orientation of the user within an environment.

Figure 9:
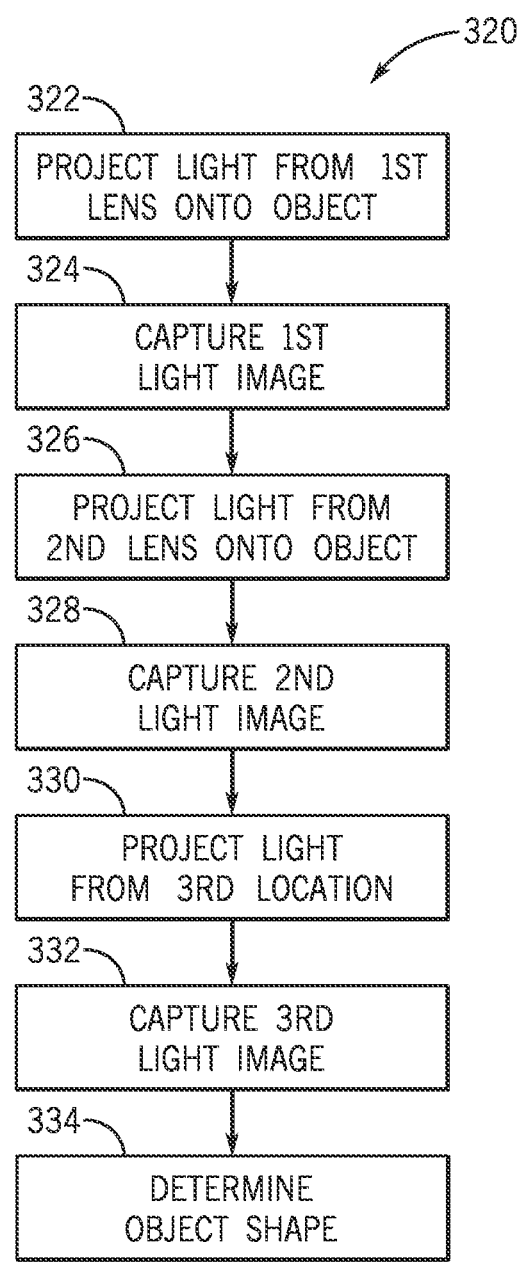
FIG. 9 is a flow chart illustrating another method of utilizing the bionic lens system to determine object characteristics.

In another example, the system may use the projected light from the lens 104 to illuminate the environment or an object from different positions, allowing the object's features to be determined from the variations in the light and shadows and comparing those changes across the different light positions. FIG. 9 illustrates a method 320 using lighting variations to determine object shape. With reference to FIG. 9, the method 320 may begin with the lens 104 projecting light (either directly or via an eye as a projector system) onto an object from a first position. In one example, this first position is the position of the first lens 104 as worn by the user, such as the right or left lens. The method 320 then proceeds to operation 324 and a first light image is captured, the first image corresponding to the illumination of the object by a first light source, in this case the first lens 104.

The method 320 then proceeds to operation 326 and light is projected onto the object from the second lens 104, e.g., the other of the right or the left eye. In this manner, the light is projected from a different angle, e.g. offset from the first image at least by the inter-pupillary distance or other distance between the two lenses 104. In another example, the user may actually tilt his or her head or body position relative to the object and the same lens that captured the first image may capture the second image from the same viewpoint, but with the light reflecting from the object at a different position. As the light is being projected onto the object from the second angle, the lens 104 captures a second light image.

The method 320 may then repeat the projection and capturing operations 330, 332 with the light source at a third or more position. The additional positions may be generated by using additional light sources, such as a view from a different head position, ambient lights, mobile phone, headphones, or a wearable accessory including a light source, that projects from a location other than one of the user's eyes or by having the user physically tilt his or her head or eyes to another orientation relative to the object.

For example, the user can tilt his or her head as various images are captured, the titled position of the head acts to vary the angle of the bionic lenses relative to the object to define a third location. In this example, the captured images may need to be pre-processed before being used to determine the object characteristics to correct for the tilt of the head, i.e., straighten the image to a reference frame that matches an orientation of the other captured images. As a specific example, a first image is captured with the object being illuminated with light emitted from a bionic lens worn in the user's left eye with the user's head at a first orientation, a second image is captured with the object being illuminated with light emitted from a bionic lens worn in the user's right eye with the user's head in the same first orientation, and then a third image is captured with the user's head titled at 45 degrees counter clockwise relative to the object and being illuminated by one of or both the right lens or the left lens. The three or more images can then be analyzed to determine various characteristics of the object. In various examples, the system may also include an external sensor that tracks or determines the user's head position, allowing the system to more easily compensate the captured images in light of the head position, e.g., a gyroscope, inertial measurement unit, gyro, global positioning element, or the like. In one example, the external positioning sensor may be located in headphones or ear buds worn by the user or on another head mounted module.

Utilizing the three or more light positions and corresponding light images, the method 320 proceeds to operation 334 and a processor or computer determines the shape of the object based on the different lighting and shading characteristics in the difference light source conditions images. For example, the different images from the light directions will include brightness and angle incident variations that can be used to populate a lookup table or other mapping structure, to determine normal angles of the object's surface. Using the determined normal values from the light angles, the processor can integrate the various normal to output a surface value and shape.

Gaze Detection and Data Transfer

The bionic lens 104 system can be used to assist in gaze detection, which can be used in many applications to vary outputs or provide different user experiences based on gaze direction and orientation. In one example, a projector-camera system can be used to include one projected light display, which may be a spotlight or collimated beams, and a camera in the other lens to capture the location of the projected light. The location of the projected light can then be correlated to the direction of the user's gaze, since the bionic lens 104 may generally move with movement of the user's eye 102 and head, such that as a user looks around, the projected light beam may be moved correspondingly. The projected beam or spotlight may also be modulated to be specific to the user or the specific lens 104 within the user, e.g., right lens or left lens, to allow determination of the gaze direction for a specific eye. If a single lens is used, the gaze direction of one eye including the lens light beam may be considered to be the same as the other eye.

Additionally, a gaze or focus point for the user's eyes can be estimated. FIG. 10A illustrates a method to determine a focus location, the method 400 includes activating a light source from a bionic lens 104, either from the bionic lens' display, imaged onto and reflected off the retina, then projected into space by the user's lens, and/or from a front facing display and lens (projector) on the bionic lens 104. The light source may be modulated, colored, or otherwise identifiable as corresponding to a particular lens 104 such that the light source can be matched to a particular eye of the user. In some examples, the user wears a bionic lens 104 in each eye and the two lenses 104 emit a modulated light, allowing a first light source to be identified as corresponding to the first eye and a second light source to be identified as corresponding to the second eye. For example, as shown in FIG. 10B, a first light source 255*a* is projected by a first bionic lens 104 and a second light source 255*b* is projected by a second bionic lens, the light sources 255*a*, 255*b* emitting light that reflects onto a surface 253.

Figure 10C:
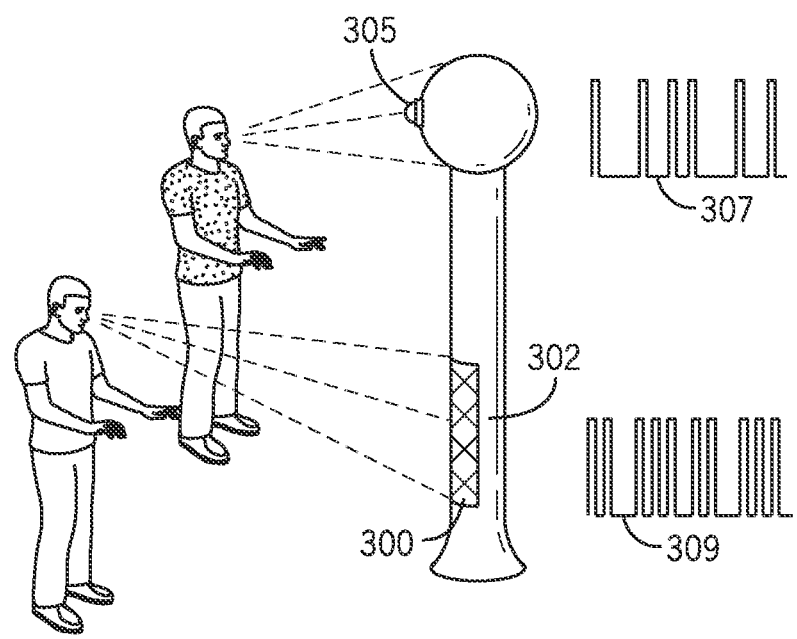
FIG. 10C is a schematic of a system using light characteristics emitted by the bionic lens detected by an object to generate individualized user experiences.

The method 400 then proceeds to operation 404 and the projected light beams are detected. For example, external image sensors or light sensors may be used in certain environments that detect the light beams and determine the location of the projected beam, e.g., location of light spots 255*a*, 255*b* on surface 253 (shown in FIG. 10C) such as an object onto which the beam is reflected, correlating that location to the gaze location. In some instances, the more general gaze area may be used and the method 400 may terminate. However, in some instances a more specific focus area may be desired. In these instances, the method 400 proceeds to operation 406 and a beam crossing location, e.g., location 257, for the left eye lens 104 beam and the right eye lens 104 beam is determined. For example, the crossing point of the two light beams can be determined via beam tracing in the 3D space surrounding the user and geometric analysis can be used to determine the cross point. In particular, as shown in FIG. 10B, the lights 255*a*, 255*b* are traced from the known projection point of the bionic lenses 104 by identifying the characteristics of the two lights 255*a*, 255*b*, their location on the object 253, and tracing the beams back to determine where the beams cross 257.

The beam crossing point can be determined to be at a particular location in 3D space and/or object in the user environment and estimated as being the focus point for the user. For example, the convergence point 257 of the beams 255*a*, 255*b* in FIG. 10B may be correlated to a focus location of the user. The focus or gaze information in operation 408 may be output to a corresponding user device, computer, other element that utilizes the gaze information to provide an interactive experience for the user or vary the information and images displayed or output to the user, either in the environment or otherwise. The gaze and focus information can be used to generate user specific outputs, such as in an immersive interactive environment, certain objects may be "smart" and interact with the user as the user is focused on the object (as determined by the method 400). In this example, the object could display a user specific output (e.g., happy birthday Bob!), light up in a specific color, or generate another type of individualized experience for the user. That is, the light beams may be modulated or otherwise include user data that can be detected by objects within the environment.

More specifically, the light beams generated and projected by the bionic lens 104 may include data, the light beams can be modulated similarly to a carrier wave with data overlaid, to transmit data between the lens 104 and other computing devices, such as smart objects, or the like. The data could them be transmitted from a user device (e.g., smartphone) in communication with the bionic lenses 104 to another computing device, such as a smart object, another user phone or computing device, or the like. In some instances, the exchange of data via the bionic lens 104 may be determined based on a detected gaze or focus location, e.g., focusing on a particular object (detectable via the method 400 of FIG. 10A) provides an input to the system that triggers the release of certain data via the modulated light beams from the bionic lens 104.

For example, FIG. 10D illustrates a system where an object 302 receives light from a first user and a second user, where the first user projects a first light pattern 307 having a first identifying set of characteristics (e.g., modulated light) and the second user projects a second light pattern 309 have another different set of characteristics (e.g., modulated light) that allows the object 302 or other element to determine the differences between light from the first user's bionic lens and the second user's bionic lens. In one embodiment, the first light pattern has a first emitting pattern and the second light pattern has a second emitting pattern different from the first one. Additionally or alternatively, the light wavelengths may be different from one another to also distinguish between the two users.

In other instances, the bionic lens 104 and the light projected either directly outwards or via the reflection from the user's retina 112, can be used to identify a user or gaze information or allow auxiliary devices to more easily detect the user's eye location. For example, the bionic lens 104 may act to "glow" or illuminate the pupil (with either visible or invisible wavelengths) and the light, which may be more easily detected than a pupil location, can be tracked by auxiliary devices, allowing a more accurate and simplified gaze tracking. This can be used to assist in increasing accuracy for performance capture for computer animation and other techniques. Current performance tracking techniques that convert a person's physical motions into animated motion may not accurately or easily capture the person's eye movements. Utilizing the emitted glow or light from the bionic lens 104, systems can identify and track the motion and movements of the person's eyes, allowing this motion to be more easily converted to the computer animation realm.

Health Detection and Identification

The bionic lens 104 can be used to detect certain user characteristics that can be used to allow proper identification of the lens with the user (e.g., correct lenses for the particular person and/or correct lens for the correct eye, right or left). In some instances, the bionic lens 104 can capture data corresponding to the user's eye and use the biometric information to validate the operation of the lenses and/or provide errors or alerts in the event that the lenses are interested into the eyes of a different user or in the wrong eye for the specific lens 104.

Figure 11:
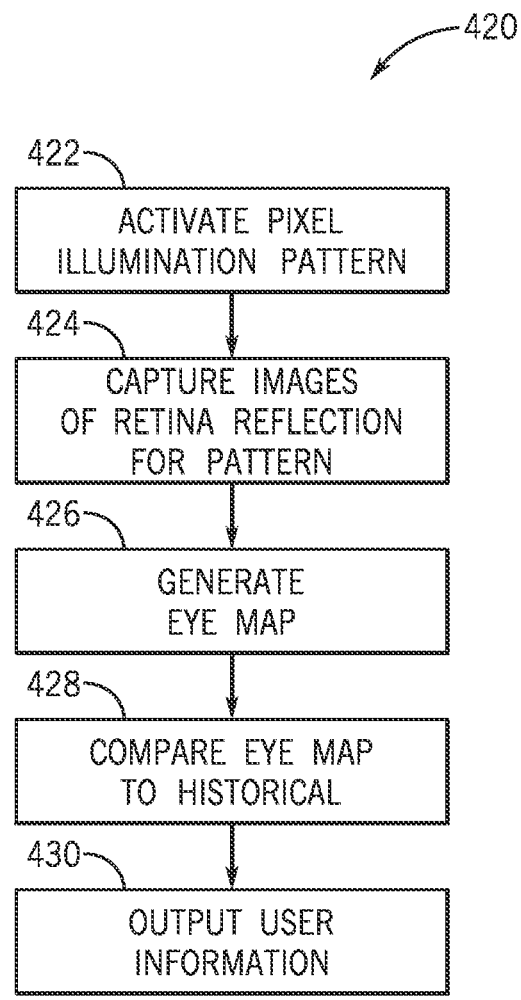
FIG. 11 is a flow chart illustrating a method to determine user specific information via the bionic lens system.

One example of biometric information that may be used is a retinal scan. FIG. 11 illustrates a method 420 to generate a biometric map for the user's eye utilizing the bionic lens 104. The method 420 includes activating a pixel illumination pattern to be displayed by the display 116 of the lens 104. The pixel illumination pattern may include a scan type of pattern, where rows of pixels are sequentially illuminated, grayscale patterns, or may be another type of pixel or group of pixels illuminated pattern. As the pattern is activated sequentially, the image sensor 118 or an external sensor captures images of the retina 112 (either directly or via a reflective surface, such as a mirror or white surface), such that the captured retina images correspond to a particular point in the pattern, e.g., first row, first pixel illuminated, or the like.

Utilizing the captured images, along with the known characteristics of the pattern and its sequential illumination, the method 420 proceeds to operation 426 and a processor or other computing element generates an eye or retinal map. The retinal map may include a correspondence of bright or dark spots or average light reflected from the retina at various points during the pattern's illumination sequence. Due to the different retinal structures, veins, and the like, the light reflectance from the retina may be different or unique for each user, allowing the retinal map to be uniquely generated for each user and each user's specific eye, e.g., left eye or right eye.

Alternatively, an image of the retina may be captured in a single image using the onboard sensors of the bionic lens 104. For example, external lights may illuminate the u retina 112, causing the light to reflect off the retina, the reflected retinal light is then imaged onto the LED array by the biological lens 110 and bionic lens 104, with the LED array or other display 116 configured to sense light rather than emit light. In other embodiments, an inward facing image sensor of the bionic lens may capture an image of the retina directly.

In some instances, the retina map may be compared to historical maps, such as in operation 428. In these instances, the historical retinal map may be compared to a current retinal map to determine if the lens 104 is inserted into the proper eye and/or if the lens 104 is being worn by the designated user. As another example, the retinal maps can be used to determine if the bionic lens 104 is inserted properly, as the light from the display 116 may reflect from the retina 112 differently, generating slightly different retinal maps, based on the positon of the lens 104 relative to the cornea.

The method 420 may also include operation 430 where a user output is provide based on the comparison in operation 428. For example, the lens 104 may display a green light or other image that corresponds to a validated comparison, e.g., the bionic lens 104 is inserted into the correct eye or correct user. In other examples, the comparison can be used to determine health information for the user, e.g., detect changes in veins or other structures within the user's eye. In these instances, the user output may include a display regarding health information or warnings, e.g., health alerts regarding possible hemorrhages, oxygen levels, pulse, blood pressure, blood alcohol content, and the like. The comparison can also be used to determine whether the bionic lens 104 has been inserted onto the cornea in the correct orientation or position, such as by comparing the locations of certain retinal features in the current scan as compared to historical scans. The user output may then include specific orientation adjustments, e.g., move lens up and to the right, etc. In some embodiments, the biometric information detected or captured via method 420 can also be used as part of the data transferred via the light modulation to identify specific users.

CONCLUSION

The methods and systems are described herein with reference to certain applications for bionic contact lenses. However, these techniques are equally applicable to other types applications utilizing displays or sensors inserted onto a user's eye. In methodologies directly or indirectly set forth herein, various steps and operations are described in one possible order of operation but those skilled in the art will recognize the steps and operation may be rearranged, replaced or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method to determine eye characteristics of a user wearing one or more bionic lenses comprising:
   capturing by a first bionic lens worn in a first eye of the user a first image corresponding to a calibration pattern positioned at a first relative orientation of the calibration pattern to the user;
   capturing by the first bionic lens a second image corresponding to the calibration pattern positioned at a second relative orientation of the calibration pattern to the user; and
   analyzing the first image and the second image by a processor to determine the eye characteristics of the user by:
      comparing a known characteristic of the calibration pattern to a characteristic of a representation of the calibration pattern in the first image and the second image; and
      determining a difference between the known characteristic and the characteristic of the representation of the calibration pattern.

2. A method to determine eye characteristics of a user wearing one or more bionic lenses comprising:
   capturing by a first bionic lens worn in a first eye of the user a first image corresponding to a calibration pattern positioned at a first relative orientation of the calibration pattern to the user;
   capturing by the first bionic lens a second image corresponding to the calibration pattern positioned at a second relative orientation of the calibration pattern to the user;
   analyzing the first image and the second image by a processor to determine the eye characteristics of the user;
   capturing by a second bionic lens worn in a second eye of the user a third image corresponding to the calibration pattern positioned at the first relative orientation to the user;
   capturing by the second bionic lens a fourth image corresponding to the calibration pattern positioned at the second relative orientation to the user; and
   analyzing the first image, the second image, the third image, and the forth image to determine an eye spacing between the first eye of the user and the second eye of the user.

3. The method of claim 2, wherein analyzing the first image, the second image, the third image, and so on up to an Nth image to determine an eye spacing includes estimating a camera distance between the first bionic lens and the second bionic lens.

4. The method of claim 1, wherein the first orientation corresponds to the user looking in a first direction toward the calibration pattern and the second orientation corresponds to the user looking in a second direction toward the calibration pattern.

5. The method of claim 1, wherein the first orientation corresponds to a first location of the calibration pattern relative to the user and the second orientation corresponds to a second location of the calibration pattern relative to the user.

6. The method of claim 5, wherein:
the calibration pattern is displayed on a display;
the first location of the calibration pattern corresponds to a first portion of the display; and
the second location of the calibration pattern corresponds to a second portion of the display.

7. The method of claim 1, wherein the bionic lens comprises an onboard display, and the method further comprises displaying the calibration pattern on the onboard display, wherein one of the first image or the second image includes a light reflected from the first eye.

8. The method of claim 1, wherein the characteristic of the representation is at least one of a translation, a rotation, or an extrinsic characteristic of the first image or the second image.

9. The method of claim 1, further comprising analyzing the difference between the known characteristic and the characteristic of the representation of the calibration pattern to determine that a quality of the bionic lens satisfies a manufacturing standard.

10. The method of claim 2, wherein analyzing the first image and the second image comprises analyzing a model of a human interpupillary distance between the first eye of the user and the second eye of the user.

11. The method of claim 1, wherein the eye characteristics comprise at least one of a pivot point, a rotational axis of the bionic lens relative to the first eye, or a center of rotation of the first eye.

12. The method of claim 1, further comprising analyzing the first image and the second image to determine a center of rotation of a head of the user.

13. The method of claim 1, wherein the first bionic lens includes an integral image sensor configured to capture the first image and the second image.

14. The method of claim 1, wherein the calibration pattern comprises a structured light pattern.

15. A system to determine eye characteristics of a user wearing one or more bionic lenses comprising:
a first bionic lens configured to be worn in a first eye of the user; and
a processing element in communication with the first bionic lens, wherein the processing element is configured to:
capture by the first bionic lens a first image corresponding to a calibration pattern positioned at a first relative orientation of the calibration pattern to the user,
capture by the first bionic lens a second image corresponding to the calibration pattern positioned at a second relative orientation of the calibration pattern to the user, and
analyze the first image and the second image to determine the eye characteristics of the user by:
comparing a known characteristic of the calibration pattern to a characteristic of a representation of the calibration pattern in the first image and the second image; and
determining a difference between the known characteristic and the characteristic of the representation of the calibration pattern.

16. The system of claim 15, further comprising:
a second bionic lens configured to be worn in a second eye of the user, wherein the processing element is further configured to:
capture by the second bionic lens a third image corresponding to the calibration pattern positioned at the first relative orientation to the user,
capture by second bionic lens a fourth image corresponding to the calibration pattern positioned at the second relative orientation to the user, and
analyze the first image, the second image, the third image, and the forth image to determine an eye spacing between the first eye of the user and the second eye of the user.

17. The system of claim 16, wherein analyzing the first image, the second image, the third image, and so on up to an Nth image to determine an eye spacing includes estimating a camera distance between the first bionic lens and the second bionic lens.

18. The system of claim 1, wherein the first orientation corresponds to the user looking in a first direction toward the calibration pattern and the second orientation corresponds to the user looking in a second direction toward the calibration pattern.

19. The method of claim 1, wherein the first orientation corresponds to a first location of the calibration pattern relative to the user and the second orientation corresponds to a second location of the calibration pattern relative to the user.

* * * * *